US011278437B2

(12) United States Patent
Christianson et al.

(10) Patent No.: US 11,278,437 B2
(45) Date of Patent: Mar. 22, 2022

(54) COMPRESSION CAPABLE ANNULAR FRAMES FOR SIDE DELIVERY OF TRANSCATHETER HEART VALVE REPLACEMENT

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US)

(73) Assignee: VDyne, Inc., Maple Grove, MN (US)

( * ) Notice: Subject to any disclaimer, the term of this patent is extended or adjusted under 35 U.S.C. 154(b) by 64 days.

(21) Appl. No.: 16/449,420

(22) Filed: Jun. 23, 2019

(65) Prior Publication Data
US 2020/0179146 A1 Jun. 11, 2020

Related U.S. Application Data

(60) Provisional application No. 62/777,070, filed on Dec. 8, 2018.

(51) Int. Cl.
*A61F 2/95* (2013.01)
*A61F 2/24* (2006.01)
(Continued)

(52) U.S. Cl.
CPC .......... *A61F 2/95* (2013.01); *A61B 17/00234* (2013.01); *A61F 2/2418* (2013.01);
(Continued)

(58) Field of Classification Search
CPC ...... A61F 2/2427; A61F 2/243; A61F 2/2436; A61F 2/2439; A61F 2/95; A61F 2/9522; A61F 2/966; A61F 2002/9665
See application file for complete search history.

(56) References Cited

U.S. PATENT DOCUMENTS 3,744,060 A 7/1973 Bellhouse et al.
4,079,468 A 3/1978 Liotta et al.
(Continued)

FOREIGN PATENT DOCUMENTS

AU 2006203686 B2 11/2008
AU 2009219415 A1 9/2009
(Continued)

OTHER PUBLICATIONS

International Search Report and Written Opinion for International Application No. PCT/US2019/028822, dated Oct. 24, 2019, 14 pages.
(Continued)

*Primary Examiner* — Diane D Yabut

(57) ABSTRACT

The invention relates to a transcatheter heart valve replacement (A61F2/2412), and in particular Compression Capable Annular Frames for a side delivered transcatheter prosthetic heart valve having a annular support frame having compressible wire cells that facilitate rolling and folding the valve length-wise, or orthogonally to the central axis of the flow control component, allowing a very large diameter valve to be delivered and deployed to the tricuspid valve from the inferior vena cava or superior vena cava, or trans-atrially to the mitral valve, the valve having a height of about 5-60 mm and a diameter of about 25-80 mm, without requiring an oversized diameter catheter and without requiring delivery and deployment from a catheter at an acute angle of approach.

18 Claims, 24 Drawing Sheets

(51) Int. Cl.
  *A61F 2/92* (2013.01)
  *A61F 2/91* (2013.01)
  *A61B 17/00* (2006.01)

(52) U.S. Cl.
  CPC .......... *A61F 2/2427* (2013.01); *A61F 2/2436* (2013.01); *A61F 2/91* (2013.01); *A61F 2/92* (2013.01); *A61B 2017/00243* (2013.01); *A61B 2017/00292* (2013.01); *A61B 2017/00305* (2013.01); *A61B 2017/00323* (2013.01); *A61F 2/9522* (2020.05); *A61F 2210/0014* (2013.01); *A61F 2220/0008* (2013.01); *A61F 2240/001* (2013.01)

(56) References Cited

U.S. PATENT DOCUMENTS

| | | | |
|---|---|---|---|
| 5,397,351 | A | 3/1995 | Pavcnik et al. |
| 5,509,428 | A | 4/1996 | Dunlop |
| 5,554,185 | A | 9/1996 | Block et al. |
| 6,006,134 | A | 12/1999 | Hill et al. |
| 6,197,013 | B1 | 3/2001 | Reed et al. |
| 6,290,719 | B1 | 9/2001 | Garberoglio |
| 6,449,507 | B1 | 9/2002 | Hill et al. |
| 6,458,153 | B1 | 10/2002 | Bailey et al. |
| 6,532,388 | B1 | 3/2003 | Hill et al. |
| 6,582,467 | B1 | 6/2003 | Teitelbaum et al. |
| 6,628,987 | B1 | 9/2003 | Hill et al. |
| 6,669,724 | B2 | 12/2003 | Park et al. |
| 6,718,208 | B2 | 4/2004 | Hill et al. |
| 6,769,434 | B2 | 8/2004 | Liddicoat et al. |
| 6,890,330 | B2 | 5/2005 | Streeter et al. |
| 6,896,690 | B1 | 5/2005 | Lambrecht et al. |
| 6,904,318 | B2 | 6/2005 | Hill et al. |
| 6,929,653 | B2 | 8/2005 | Streeter |
| 7,074,189 | B1 | 7/2006 | Montegrande |
| 7,125,418 | B2 | 10/2006 | Duran et al. |
| 7,175,660 | B2 | 2/2007 | Cartledge et al. |
| 7,201,761 | B2 | 4/2007 | Woolfson et al. |
| 7,225,019 | B2 | 5/2007 | Jahns et al. |
| 7,269,457 | B2 | 9/2007 | Shafer et al. |
| 7,331,991 | B2 | 2/2008 | Kheradvar et al. |
| 7,361,189 | B2 | 4/2008 | Case et al. |
| 7,374,571 | B2 | 5/2008 | Pease et al. |
| 7,442,204 | B2 | 10/2008 | Schwammenthal et al. |
| 7,449,027 | B2 | 11/2008 | Hunt et al. |
| 7,621,948 | B2 | 11/2009 | Herrmann et al. |
| 7,648,527 | B2 | 1/2010 | Agnew |
| 7,717,952 | B2 | 5/2010 | Case et al. |
| 7,749,245 | B2 | 7/2010 | Cohn et al. |
| 7,753,949 | B2 | 7/2010 | Lamphere et al. |
| 7,811,316 | B2 | 10/2010 | Kalmann et al. |
| 7,828,840 | B2 | 11/2010 | Biggs et al. |
| 7,846,199 | B2 | 12/2010 | Paul, Jr. et al. |
| 8,303,648 | B2 | 11/2012 | Grewe et al. |
| 8,366,768 | B2 | 2/2013 | Zhang |
| 8,491,650 | B2 | 7/2013 | Wiemeyer et al. |
| 8,568,474 | B2 | 10/2013 | Yeung et al. |
| 8,628,571 | B1 | 1/2014 | Hacohen et al. |
| 8,641,752 | B1 | 2/2014 | Holm et al. |
| 8,696,743 | B2 | 4/2014 | Holecek et al. |
| 8,728,153 | B2 | 5/2014 | Bishop et al. |
| 8,758,395 | B2 | 6/2014 | Kleshinski et al. |
| 8,846,390 | B2 | 9/2014 | Dove et al. |
| 8,876,892 | B2 | 11/2014 | Tran et al. |
| 8,900,295 | B2 | 12/2014 | Migliazza et al. |
| 8,915,958 | B2 | 12/2014 | Braido |
| 8,926,690 | B2 | 1/2015 | Kovalsky |
| 8,926,692 | B2 | 1/2015 | Dwork |
| 8,926,694 | B2 | 1/2015 | Costello |
| 8,940,044 | B2 | 1/2015 | Hammer et al. |
| 8,956,404 | B2 | 2/2015 | Bortlein et al. |
| 8,986,370 | B2 | 3/2015 | Annest et al. |
| 9,011,524 | B2 | 4/2015 | Eberhardt |
| 9,017,399 | B2 | 4/2015 | Gross et al. |
| 9,050,188 | B2 | 6/2015 | Schweich, Jr. et al. |
| 9,072,604 | B1 | 7/2015 | Melnick et al. |
| 9,119,714 | B2 | 9/2015 | Shandas et al. |
| 9,216,076 | B2 | 12/2015 | Mitra et al. |
| 9,232,995 | B2 | 1/2016 | Kovalsky et al. |
| 9,241,792 | B2 | 1/2016 | Benichou et al. |
| 9,248,016 | B2 | 2/2016 | Oba et al. |
| 9,259,215 | B2 | 2/2016 | Chou et al. |
| 9,277,990 | B2 | 3/2016 | Klima et al. |
| 9,289,282 | B2 | 3/2016 | Olson et al. |
| 9,289,296 | B2 | 3/2016 | Braido et al. |
| 9,295,547 | B2 | 3/2016 | Costello et al. |
| 9,301,839 | B2 | 4/2016 | Stante et al. |
| 9,308,086 | B2 | 4/2016 | Ho |
| 9,339,367 | B2 | 5/2016 | Carpenter et al. |
| 9,370,418 | B2 | 6/2016 | Pintor et al. |
| 9,381,083 | B2 | 7/2016 | Costello |
| 9,387,075 | B2 | 7/2016 | Bortlein et al. |
| 9,393,111 | B2 | 7/2016 | Ma et al. |
| 9,414,915 | B2 | 8/2016 | Lombardi et al. |
| 9,433,500 | B2 | 9/2016 | Chau et al. |
| 9,440,054 | B2 | 9/2016 | Bishop et al. |
| 9,456,899 | B2 | 10/2016 | Yeung et al. |
| 9,468,525 | B2 | 10/2016 | Kovalsky et al. |
| 9,474,604 | B2 | 10/2016 | Centola et al. |
| 9,486,306 | B2 | 11/2016 | Tegels et al. |
| 9,510,941 | B2 | 12/2016 | Bishop et al. |
| 9,554,902 | B2 | 1/2017 | Braido et al. |
| 9,579,196 | B2 | 2/2017 | Morriss et al. |
| 9,579,200 | B2 | 2/2017 | Lederman et al. |
| 9,610,159 | B2 | 4/2017 | Christianson et al. |
| 9,615,925 | B2 | 4/2017 | Subramanian et al. |
| 9,629,719 | B2 | 4/2017 | Rothstein |
| 9,636,222 | B2 | 5/2017 | Oslund |
| 9,649,191 | B2 | 5/2017 | Savage et al. |
| 9,662,202 | B2 | 5/2017 | Quill et al. |
| 9,662,203 | B2 | 5/2017 | Sheahan et al. |
| 9,662,209 | B2 | 5/2017 | Gross et al. |
| 9,675,454 | B2 | 6/2017 | Vidlund et al. |
| 9,675,485 | B2 | 6/2017 | Essinger et al. |
| 9,687,343 | B2 | 6/2017 | Bortlein et al. |
| 9,707,076 | B2 | 7/2017 | Stack et al. |
| 9,713,530 | B2 | 7/2017 | Cabiri et al. |
| 9,750,607 | B2 | 9/2017 | Ganesan et al. |
| 9,763,778 | B2 | 9/2017 | Eidenschink et al. |
| 9,763,779 | B2 | 9/2017 | Bortlein et al. |
| 9,788,946 | B2 | 10/2017 | Bobo, Jr. et al. |
| 9,839,511 | B2 | 12/2017 | Ma et al. |
| 9,849,011 | B2 | 12/2017 | Zimmerman et al. |
| 9,855,384 | B2 | 1/2018 | Cohen et al. |
| 9,861,464 | B2 | 1/2018 | Azimpour et al. |
| 9,895,219 | B2 | 2/2018 | Costello |
| 9,901,330 | B2 | 2/2018 | Akpinar |
| 9,918,838 | B2 | 3/2018 | Ring |
| 9,943,409 | B2 | 4/2018 | Kim et al. |
| 9,949,825 | B2 | 4/2018 | Braido et al. |
| 9,968,444 | B2 | 5/2018 | Millwee et al. |
| 9,968,445 | B2 | 5/2018 | Kheradvar |
| 9,980,815 | B2 | 5/2018 | Nitzan et al. |
| 9,987,121 | B2 | 6/2018 | Blanzy |
| 10,010,411 | B2 | 7/2018 | Peter |
| 10,010,412 | B2 | 7/2018 | Taft et al. |
| 10,022,054 | B2 | 7/2018 | Najafi et al. |
| 10,022,222 | B2 | 7/2018 | Groothuis et al. |
| 10,022,223 | B2 | 7/2018 | Bruchman |
| 10,028,821 | B2 | 7/2018 | Centola et al. |
| 10,028,831 | B2 | 7/2018 | Morin et al. |
| 10,034,667 | B2 | 7/2018 | Morris et al. |
| 10,034,747 | B2 | 7/2018 | Harewood |
| 10,039,638 | B2 | 8/2018 | Bruchman et al. |
| 10,058,315 | B2 | 8/2018 | Rafiee et al. |
| 10,058,411 | B2 | 8/2018 | Fifer et al. |
| 10,058,421 | B2 | 8/2018 | Eberhardt et al. |
| 10,058,426 | B2 | 8/2018 | Barbarino |
| 10,064,405 | B2 | 9/2018 | Dale et al. |
| 10,080,653 | B2 | 9/2018 | Conklin et al. |
| 10,085,835 | B2 | 10/2018 | Thambar et al. |
| 10,105,224 | B2 | 10/2018 | Buchbinder et al. |
| 10,117,741 | B2 | 11/2018 | Schweich, Jr. et al. |

(56) References Cited

U.S. PATENT DOCUMENTS

| | | |
|---|---|---|
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,333 B2 | 3/2019 | Cartledge |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 | 5/2020 | Vidlund et al. |
| 10,758,346 B1 | 9/2020 | Christianson et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund et al. |
| 11,173,027 B2 | 11/2021 | Christianson et al. |
| 2003/0040772 A1 | 2/2003 | Hyodoh |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 | 8/2006 | Kheradvar et al. |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1* | 10/2007 | Nguyen .............. A61F 2/9525 623/2.11 |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere |
| 2008/0221672 A1 | 9/2008 | Lamphere et al. |
| 2008/0262592 A1 | 10/2008 | Jordan et al. |
| 2008/0262609 A1 | 10/2008 | Gross |
| 2008/0275550 A1 | 11/2008 | Kheradvar et al. |
| 2009/0005863 A1 | 1/2009 | Goetz et al. |
| 2009/0054976 A1* | 2/2009 | Tuval .............. A61F 2/2415 623/2.11 |
| 2009/0094189 A1 | 4/2009 | Stephens |
| 2009/0192586 A1 | 7/2009 | Tabor |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung |
| 2011/0125145 A1 | 5/2011 | Mody |
| 2011/0137397 A1 | 6/2011 | Chau et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson |
| 2012/0022639 A1 | 1/2012 | Hacohen et al. |
| 2012/0022640 A1 | 1/2012 | Gross |
| 2012/0022644 A1 | 1/2012 | Reich |
| 2012/0035701 A1 | 2/2012 | To |
| 2012/0065723 A1 | 3/2012 | Drasler et al. |
| 2012/0083874 A1* | 4/2012 | Dale .............. A61F 2/2427 623/2.11 |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge |

(56) References Cited

U.S. PATENT DOCUMENTS

| | | |
|---|---|---|
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1 | 11/2013 | McLean et al. |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1 | 1/2014 | Buchbinder et al. |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1 | 12/2014 | Vidlund |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen |
| 2015/0230919 A1 | 8/2015 | Chau |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini |
| 2015/0282922 A1 | 10/2015 | Hingston et al. |
| 2015/0282931 A1 | 10/2015 | Brunnett et al. |
| 2015/0289971 A1 | 10/2015 | Costello |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1 | 2/2016 | Morriss et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo |
| 2016/0095703 A1 | 4/2016 | Thomas et al. |
| 2016/0095704 A1 | 4/2016 | Whitman |
| 2016/0113764 A1 | 4/2016 | Sheahan |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |

(56) References Cited

U.S. PATENT DOCUMENTS

| | | |
|---|---|---|
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust |
| 2017/0112620 A1 | 4/2017 | Curley et al. |
| 2017/0128208 A1 | 5/2017 | Christianson |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane |
| 2017/0209268 A1 | 7/2017 | Cunningham et al. |
| 2017/0216026 A1 | 8/2017 | Quill et al. |
| 2017/0216030 A1 | 8/2017 | Joensson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane |
| 2017/0239047 A1 | 8/2017 | Quill |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini |
| 2017/0281337 A1 | 10/2017 | Campbell |
| 2017/0281341 A1 | 10/2017 | Lim et al. |
| 2017/0296340 A1 | 10/2017 | Gross |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson |
| 2017/0348100 A1 | 12/2017 | Lane |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin |
| 2018/0116793 A1 | 5/2018 | Salahieh et al. |
| 2018/0116843 A1 | 5/2018 | Schreck et al. |
| 2018/0125642 A1 | 5/2018 | White |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1* | 7/2018 | Chambers ............ A61F 2/2436 |
| 2018/0206983 A1 | 7/2018 | Noe et al. |
| 2018/0214141 A1 | 8/2018 | Mendez |
| 2018/0221016 A1 | 8/2018 | Conklin |
| 2018/0243071 A1 | 8/2018 | Eigler |
| 2018/0243532 A1 | 8/2018 | Willard et al. |
| 2018/0256322 A1 | 9/2018 | Zhang et al. |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal |
| 2018/0289475 A1 | 10/2018 | Chung et al. |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper et al. |
| 2019/0015188 A1 | 1/2019 | Eigler |
| 2019/0021834 A1 | 1/2019 | Nir |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado |
| 2019/0060069 A1 | 2/2019 | Maimon et al. |
| 2019/0060071 A1 | 2/2019 | Lane |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab |
| 2019/0133756 A1 | 5/2019 | Zhang et al. |

(56) References Cited

U.S. PATENT DOCUMENTS

| | | |
|---|---|---|
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler |
| 2019/0262129 A1 | 8/2019 | Cooper et al. |
| 2019/0269413 A1 | 9/2019 | Yodfat et al. |
| 2019/0269504 A1 | 9/2019 | Wang |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1 | 12/2019 | Lane et al. |
| 2020/0121452 A1 | 4/2020 | Saikrishnan et al. |
| 2020/0121458 A1 | 4/2020 | Vidlund et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0244536 A1 | 8/2021 | Christianson et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | CA-2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | CA-2702615 C | 6/2017 |
| CA | 2744395 C | 8/2017 |
| CA | 2753853 A1 | 9/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | CN-103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | CN-103889472 B | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |

(56) References Cited

FOREIGN PATENT DOCUMENTS

| | | |
|---|---|---|
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | CN-103945792 B | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | CN-107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | DE-202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | EP-0902704 A1 | 3/1999 |
| EP | 1301225 A2 | 4/2003 |
| EP | 1684666 A2 | 8/2006 |
| EP | 1996246 A2 | 12/2008 |
| EP | EP-1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | EP-2400926 A2 | 1/2012 |
| EP | 2427145 A2 | 3/2012 |
| EP | 1582178 B1 | 9/2012 |
| EP | EP-1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | EP-2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | EP-3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3100701 A1 | 12/2016 |
| EP | EP-1998713 B1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | EP-3232941 A1 | 10/2017 |
| EP | 3256076 A1 | 12/2017 |
| EP | EP-3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |

(56) References Cited

FOREIGN PATENT DOCUMENTS

| | | |
|---|---|---|
| EP | 3400913 A1 | 11/2018 |
| EP | 3406224 A1 | 11/2018 |
| EP | 2555709 B1 | 12/2018 |
| EP | 3417813 A1 | 12/2018 |
| EP | EP-2555709 B1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | EP-3487420 A1 | 5/2019 |
| EP | 2560580 B1 | 6/2019 |
| EP | 3508113 A1 | 7/2019 |
| EP | 1301225 A4 | 8/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3508113 A1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | JP-2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | JP-2013523261 A | 6/2013 |
| JP | 2013543399 A | 12/2013 |
| JP | 2014501563 A | 1/2014 |
| JP | JP-2014501563 A | 1/2014 |
| JP | 2014505537 A | 3/2014 |
| JP | 5527850 B2 | 6/2014 |
| JP | 2014518697 A | 8/2014 |
| JP | 201422678 A | 9/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | JP-2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | JP-2017515609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2019134972 A | 5/2018 |
| JP | JP-6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2019131148 A1 | 10/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2018008019 A2 | 9/2010 |
| WO | WO-2010119110 A1 | 10/2010 |
| WO | WO-2011112706 A2 | 9/2011 |
| WO | WO-2011137531 A1 | 11/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |

(56) References Cited

FOREIGN PATENT DOCUMENTS

| | | |
|---|---|---|
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2016148777 A1 | 9/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2019006383 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018209302 A1 | 11/2018 |
| WO | WO-2018200531 A1 | 11/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019096033 A1 | 5/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019144036 A1 | 7/2019 |
| WO | WO-2017161204 A1 | 7/2019 |
| WO | WO-2019131148 A1 | 7/2019 |

(56) References Cited

FOREIGN PATENT DOCUMENTS

| | | |
|---|---|---|
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

Office Action for U.S. Appl. No. 16/435,687, dated Aug. 7, 2019, 19 pages.
International Search Report and Written Opinion for International Application No. PCT/US2019/051615, dated Mar. 2, 2020, 14 pages.
Office Action for U.S. Appl. No. 17/167,983, dated Apr. 13, 2021, 20 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 17/154,227, dated Mar. 29, 2021, 6 pages.
Office Action for U.S. Appl. No. 16/442,504, dated Jan. 14, 2020, 11 pages.
Office Action for U.S. Appl. No. 16/445,210, dated Jan. 28, 2021, 7 pages.
Office Action for U.S. Appl. No. 17/154,438, dated May 3, 2021, 16 pages.
International Search Report and Written Opinion for International Application No. PCT/US2021/013570, dated Apr. 1, 2021, 9 pages.
International Search Report and Written Opinion for International Application No. PCT/US2020/045195, dated Jan. 8, 2021, 18 pages.
Office Action for U.S. Appl. No. 17/193,936, dated May 27, 2021, 6 pages.
International Search Report and Written Opinion for International Application No. PCT/US2020/047162, dated Dec. 30, 2020, 9 pages.
Office Action for U.S. Appl. No. 16/443,862, dated Nov. 12, 2021, 9 pages.
Office Action for U.S. Appl. No. 17/154,227, dated Jun. 18, 2021, 8 pages.
Office Action for U.S. Appl. No. 17/167,988, dated Sep. 22, 2021, 19 pages.
Office Action for U.S. Appl. No. 17/221,547, dated Aug. 4, 2021, 11 pages.
Office Action for U.S. Appl. No. 17/221,547, dated Oct. 21, 2021, 9 pages.
Office Action for U.S. Appl. No. 17/222,182, dated Sep. 2, 2021, 23 pages.
Office Action for U.S. Appl. No. 17/222,430, dated Oct. 7, 2021, 17 pages.
Office Action for U.S. Appl. No. 17/236,219, dated Aug. 4, 2021, 17 pages.

\* cited by examiner

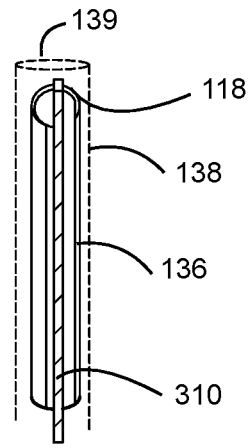
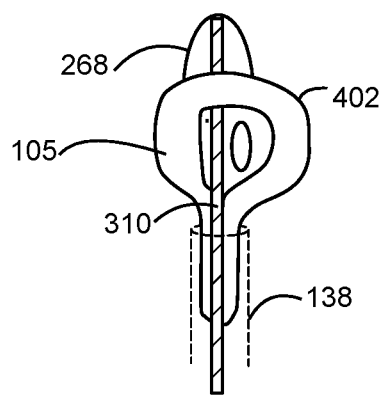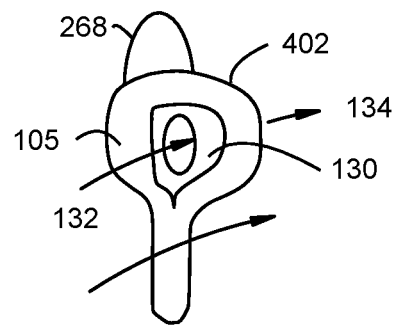
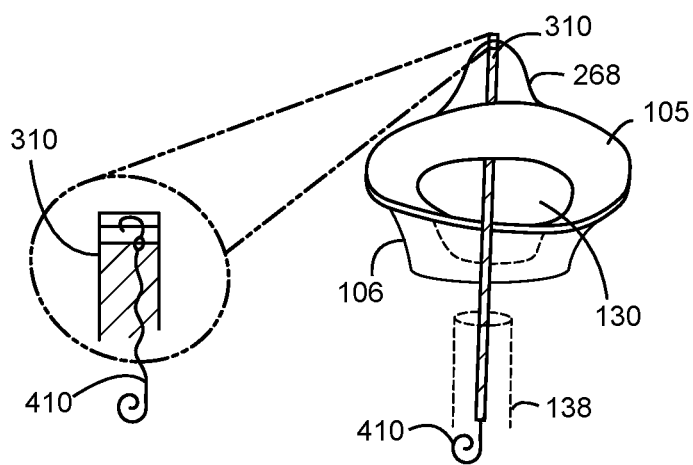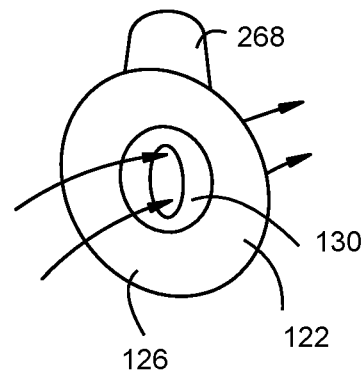

COMPRESSION CAPABLE ANNULAR FRAMES FOR SIDE DELIVERY OF TRANSCATHETER HEART VALVE REPLACEMENT

CROSS-REFERENCE TO RELATED APPLICATIONS

This application claims priority to and the benefit of U.S. Provisional Patent Application Ser. No. 62/777,070, filed Dec. 8, 2018, entitled "Compression Capable Annular Frames for Side Delivery of Transcatheter Heart Valve Replacement," the disclosure of which is incorporated herein by reference in its entirety.

BACKGROUND OF THE INVENTION

Field of the Invention

The invention relates to a transcatheter heart valve replacement (A61F2/2412).

Description of the Related Art

In 1952 surgeons implanted the first mechanical heart valve. This first valve was a ball valve and it was designed by Dr. Charles Hufnagel. The recipient of this valve was a 30-year-old woman who could lead a normal life after the surgery. However, one downside of this design was that it could only be placed in the descending aorta instead of the heart itself. For this reason it did not fully correct the valve problem, only alleviate the symptoms. However it was a significant achievement because it proved that synthetic materials could be used to create heart valves.

In 1960, a new type of valve was invented and was successfully implanted. This valve is the Starr-Edwards ball valve, named after its originators. This valve was a modification of Hufnagel's original valve. The ball of the valve was slightly smaller and caged from both sides so it could be inserted into the heart itself.

The next development was tilting disc technology which was introduced in the late 1960s. These valves were a great improvement over the ball designs. The tilting disc technology allowed blood to flow in a more natural way while reducing damage to blood cells from mechanical forces. However, the struts of these valves tended to fracture from fatigue over time. As of 2003, more than 100,000 Omniscience and 300,000 Hall-Kaster/Medtronic-Hall tilting disc valves were implanted with essentially no mechanical failure.

In 1977, bi-leaflet heart valves were introduced by St. Jude. Similar to a native heart valve, blood flows directly through the center of the annulus of pyrolytic carbon valves mounted within nickel-titanium housing which makes these valves superior to other designs. However, a downside of this design is that it allows some regurgitation. A vast majority of mechanical heart valves used today have this design. As of 2003, more than 1.3 million St. Jude valves were deployed and over 500,000 Carbomedics valves with no failures to leaflets or housing. It should be noted that the human heart beats about 31 million times per year.

Development continues with compressible valves that are delivered via a catheter instead of requiring the trauma and complications of open heart surgery. This means that a cardiologist trained in endoscopy can, in theory, deploy a heart valve replacement during an outpatient procedure. However, transcatheter valves are often delivered by perforating the apex of the heart to access the ventricle, and the perforation is often used to anchor an annular valve replacement.

Additionally, a problem with stent-style replacement valves is that they often continue to have the regurgitation or leakage problems of prior generations of valves, as well as require expensive materials engineering in order to cope with the 100's of millions of cycles encountered during just a few years of normal heart function. Accordingly, there is still a need for alternative and simpler solutions to addressing valve-related heart pathologies.

BRIEF SUMMARY OF THE INVENTION

The present invention is directed to methods and devices related to a transcatheter heart valve replacement (A61F2/2412), and in particular Compression Capable Annular Frames for a side (length-wise) delivered transcatheter prosthetic heart valve having a annular support frame having compressible wire cells that facilitate rolling and folding the valve length-wise, or orthogonal, to the central axis of the flow control component, allowing a very large diameter valve to be delivered and deployed from the inferior vena cava directly into the mitral or tricuspid valve, e.g. having a height of about 5-60 mm and a diameter of about 25-80 mm using a 24-36Fr delivery catheter, without requiring an oversized diameter catheter and without requiring delivery and deployment from a catheter at an acute angle of approach.

Method for Delivery of the Valve into a Patient

In another preferred embodiment, there is provided a method for side delivery of implantable prosthetic heart valve to a desired location in the body, the method comprising the steps:

advancing a delivery catheter to the desired location in the body and delivering an expandable prosthetic heart valve to the desired location in the body by releasing the valve from the delivery catheter, wherein advancing the delivery catheter includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach, wherein the valve comprises an annular support frame having a flow control component mounted within the annular support frame and configured to permit blood flow in a first direction through an inflow end of the valve and block blood flow in a second direction, opposite the first direction, through an outflow end of the valve, wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction, wherein the long-axis of the compressed configuration of the valve is substantially parallel to a length-wise cylindrical axis of the delivery catheter, wherein the valve has a height of about 5-60 mm and a diameter of about 25-80 mm.

In another preferred embodiment, there is provided a method for side delivery, wherein releasing the valve from the delivery catheter is selected from the steps consisting of: (i) pulling the valve out of the delivery catheter using a rigid elongated pushing rod/draw wire that is releasably connected to the distal side of the valve, wherein advancing the pushing rod away from the delivery catheter pulls the compressed valve out of the delivery catheter, or (ii) pushing the valve out of the delivery catheter using a rigid elongated pushing rod that is releasably connected to the proximal side of the valve, wherein advancing the pushing rod out of from the delivery catheter pushes the compressed valve out of the delivery catheter.

In another preferred embodiment, there is provided a method for side delivery, comprising the additional step of anchoring one or more tissue anchors attached to the valve into native tissue.

In another preferred embodiment, there is provided a method for side delivery, comprising the additional step of positioning a tension arm of the heart valve prosthesis into the right ventricular outflow tract of the right ventricle.

In another preferred embodiment, there is provided a method for side delivery, comprising the additional steps of positioning a lower tension arm of the heart valve prosthesis into the right ventricular outflow tract of the right ventricle, and positioning an upper tension arm into a supra-annular position, and the upper tension arm providing a supra-annular downward force in the direction of the ventricle and lower tension arm providing a sub-annular upward force in the direction of the atrium.

In another preferred embodiment, there is provided a method for side delivery, comprising the additional step of rotating the heart valve prosthesis using a steerable catheter along an axis parallel to the plane of the valve annulus, wherein an upper tension arm mounted on the valve is conformationally pressure locked against supra-annular tissue, and wherein a lower tension arm mounted on the valve is conformationally pressure locked against sub-annular tissue.

Method for Loading the Valve into a Delivery Catheter

In another preferred embodiment, there is provided a method for loading an implantable side-delivered prosthetic heart valve into a delivery catheter, the method comprising the steps:
loading an implantable side-delivered prosthetic heart valve into a tapering fixture or funnel attached to a delivery catheter,
wherein the valve comprises an annular support frame having a flow control component mounted within the annular support frame and configured to permit blood flow in a first direction through an inflow end of the valve and block blood flow in a second direction, opposite the first direction, through an outflow end of the valve,
wherein said loading is perpendicular or substantially orthogonal to the first direction,
wherein the valve is compressible to a compressed configuration for introduction into the body using a delivery catheter for implanting at a desired location in the body, said compressed configuration having a long-axis oriented at an intersecting angle of between 45-135 degrees to the first direction, and expandable to an expanded configuration having a long-axis oriented at an intersecting angle of between 45-135 degrees to the first direction,
wherein the long-axis of the compressed configuration of the valve is substantially parallel to a length-wise cylindrical axis of the delivery catheter,
wherein the valve has a height of about 5-60 mm and a diameter of about 25-80 mm.

In another preferred embodiment, there is provided a method for loading, wherein the step of loading includes attaching a loading accessory to a valve sidewall, to a valve cuff, to a valve tension arm, or a combination thereof, wherein the loading accessory is a pushing rod or a pulling wire, and wherein the tapering fixture or funnel has a compression element on an inner surface of the tapering fixture or funnel to facilitate compression, iris-ing, or spiraling of the uncompressed valve.

Side Delivered Valve

Accordingly, the present invention is directed to a side delivered transcatheter prosthetic heart valve, comprising:
a self-expanding annular support frame, said annular support frame having a central channel and an outer perimeter wall circumscribing a central vertical axis in an expanded configuration,
said perimeter wall having a front wall portion and a back wall portion, the front wall portion and the back wall portion connected along a proximal side to a proximal fold area, and the front wall portion and the back wall portion connected along a distal side to a distal fold area,
the front wall portion having a front upper collar portion and a front lower body portion, the back wall portion having a back upper collar portion and a back lower body portion,
said annular support frame having a flow control component mounted within the annular support frame and configured to permit blood flow in a first direction through an inflow end of the valve and block blood flow in a second direction, opposite the first direction, through an outflow end of the valve,
wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis,
wherein the horizontal axis of the compressed configuration of the valve is substantially parallel to a length-wise cylindrical axis of the delivery catheter,
wherein the valve has a height of about 5-60 mm and a diameter of about 25-80 mm.

In a preferred embodiment, the valve has an outer annular support frame that has a diameter R of 40-80 mm and a height of 5-20 mm, and the inner flow control component has a diameter of 20-35 mm.

In another preferred embodiment, the valve has a flow control component that has an internal diameter of 20-35 mm and a height of 5-30 mm, and from 2-4 leaflets of pericardial material are joined to form a rounded cylinder at an inflow end and having a closable aperture at an outflow end.

In another preferred embodiment, there is provided a side delivered transcatheter heart valve, wherein the annular support frame is comprised of a plurality of compressible wire cells having an orientation and cell geometry substantially orthogonal to the central vertical axis to minimize wire cell strain when the annular support frame is configured in a vertical compressed configuration, a rolled compressed configuration, or a folded compressed configuration.

In another preferred embodiment, there is provided a side delivered transcatheter heart valve, wherein the front lower body portion and the back lower body portion in an expanded configuration form a shape selected from a funnel, cylinder, flat cone, or circular hyperboloid.

In another preferred embodiment, there is provided a side delivered transcatheter heart valve, wherein said annular support frame is comprised of a braided, wire, or laser-cut wire frame, and said annular support frame is covered with a biocompatible material.

In another preferred embodiment, there is provided a side delivered transcatheter heart valve, wherein the annular support frame has a side profile of a flat cone shape having a diameter R of 40-80 mm, a diameter r of 20-60 mm, and a height of 5-60 mm.

In another preferred embodiment, there is provided a side delivered transcatheter heart valve, wherein the annular support frame has an inner surface and an outer surface, said inner surface and said outer surface covered with a biocompatible material selected from the following consisting of: the inner surface covered with pericardial tissue, the outer surface covered with a woven synthetic polyester material, and both the inner surface covered with pericardial tissue and the outer surface covered with a woven synthetic polyester material.

In another preferred embodiment, there is provided a side delivered transcatheter heart valve, wherein the annular support frame has a side profile of an hourglass shape having a top diameter R1 of 40-80 mm, a bottom diameter R2 of 50-70 mm, an internal diameter r of 20-60 mm, and a height of 5-60 mm.

In another preferred embodiment, there is provided a side delivered transcatheter heart valve, wherein the valve in an expanded configuration has a central vertical axis that is substantially parallel to the first direction.

In another preferred embodiment, there is provided a side delivered transcatheter heart valve, wherein the flow control component has an internal diameter of 20-60 mm and a height of 10-40 mm, and a plurality of leaflets of pericardial material joined to form a rounded cylinder at an inflow end and having a flat closable aperture at an outflow end.

In another preferred embodiment, there is provided a side delivered transcatheter heart valve, wherein the flow control component is supported with one or more longitudinal supports integrated into or mounted upon the flow control component, the one or more longitudinal supports selected from rigid or semi-rigid posts, rigid or semi-rigid ribs, rigid or semi-rigid battens, rigid or semi-rigid panels, and combinations thereof.

In another preferred embodiment, there is provided a side delivered transcatheter heart valve, comprising a tension arm extending from a distal side of the annular support frame as an RVOT tab, the tension arm comprised of wire loop or wire frame, integrated frame section, or stent, extending from about 10-40 mm away from the annular support frame.

In another preferred embodiment, there is provided a side delivered transcatheter heart valve, comprising (i) an upper tension arm attached to a distal upper edge of the annular support frame, the upper tension arm comprised of wire loop or wire frame extending from about 2-20 mm away from the annular support frame, and (ii) a lower tension arm as an RVOT tab extending from a distal side of the annular support frame, the lower tension arm comprised of wire loop or wire frame, integrated frame section, or stent, extending from about 10-40 mm away from the annular support frame.

In another preferred embodiment, there is provided a side delivered transcatheter heart valve, comprising at least one tissue anchor connected to the annular support frame for engaging native tissue.

In another preferred embodiment, there is provided a side delivered transcatheter heart valve, wherein the front wall portion is a first flat panel and the back wall portion is a second flat panel, and wherein the proximal fold area and the distal fold area each comprise a sewn seam, a fabric panel, or a rigid hinge.

In another preferred embodiment, there is provided a side delivered transcatheter heart valve, wherein the proximal fold area and the distal fold area, each comprise a flexible fabric span without any wire cells.

In another preferred embodiment, there is provided a side delivered transcatheter heart valve, wherein the annular support frame is comprised of compressible wire cells selected from the group consisting of: braided-wire cells, laser-cut wire cells, photolithography produced wire cells, 3D printed wire cells, wire cells formed from intermittently connected single strand wires in a wave shape, a zig-zag shape, or spiral shape, and combinations thereof.

Process for Manufacturing

In another preferred embodiment of the invention, there is provided a process for manufacturing a side delivered transcatheter prosthetic heart valve frame, comprising:

(i) using additive or subtractive metal or metal-alloy manufacturing to produce a self-expanding annular support frame, said annular support frame having a central channel and an outer perimeter wall circumscribing a central vertical axis in an expanded configuration, said perimeter wall having a front wall portion and a back wall portion, the front wall portion and the back wall portion connected along a proximal side to a proximal fold area, and the front wall portion and the back wall portion connected along a distal side to a distal fold area, the front wall portion having a front upper collar portion and a front lower body portion, the back wall portion having a back upper collar portion and a back lower body portion, wherein the valve is compressible to a compressed configuration for introduction into the body using a delivery catheter for implanting at a desired location in the body, said compressed configuration is oriented along a horizontal axis at an intersecting angle of between 45-135 degrees to the central vertical axis, and expandable to an expanded configuration having a horizontal axis at an intersecting angle of between 45-135 degrees to the central vertical axis, wherein the horizontal axis of the compressed configuration of the valve is substantially parallel to a length-wise cylindrical axis of the delivery catheter, wherein the additive metal or metal-alloy manufacturing is 3D printing or direct metal laser sintering (powder melt), and wherein the subtractive metal or metal-alloy manufacturing is photolithography, laser sintering/cutting, CNC machining, electrical discharge machining, and wherein the valve frame has a height of about 5-60 mm and a diameter of about 25-80 mm.

In another preferred embodiment, there is provided a process for manufacturing a side delivered transcatheter prosthetic heart valve frame, further comprising the steps of:
(ii) mounting a flow control component within the valve frame, said flow control component configured to permit blood flow along the central vertical axis through an inflow end of the flow control component and block blood flow through an outflow end of the valve,
(iii) covering an outer surface of the valve frame with a pericardium material or similar biocompatible material.

Method for Compressing the Valve

In another preferred embodiment, there is provided a method for compressing an implantable prosthetic heart valve for length-wise orthogonal release of the valve from a delivery catheter, comprising the steps:

flattening, rolling or folding the implantable prosthetic heart valve into a compressed configuration wherein the long-axis of the compressed configuration of the valve is substantially parallel to a length-wise cylindrical axis of the delivery catheter, wherein the implantable prosthetic heart valve comprises an annular support frame having a flow control component mounted within the annular support frame and configured to permit blood flow in a first direction through an inflow end of the valve and block blood flow in a second direction, opposite the first direction, through an outflow end of the valve, wherein the valve has a height of about 5-60 mm and a diameter of about 25-80 mm.

In another preferred embodiment, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.

Method for Improving Blood Flow Transition During Implantation

In another preferred embodiment, there is provided a method for improving hemodynamic flow during implantation of a transcatheter prosthetic heart valve, comprising:
advancing a delivery catheter to the desired location in the body and delivering the valve of claim 1 to the desired location in the body;
partially releasing the valve from the delivery catheter to establish blood flow around the partially released valve and establish blood flow through the flow control component;
completely releasing the valve from the delivery catheter while maintaining attachment to the valve with a positioning catheter or wire to transition to increased blood flow through the flow control component and decreasing blood flow around the valve; and
deploying the valve into a final mounted position to transition to complete blood flow through the flow control component and minimal or no blood flow around the valve, and disconnecting and withdrawing the positioning catheter or wire from the valve.

In another preferred embodiment, there is provided a method of improving hemodynamic flow, wherein the RVOT tab is in the RVOT during the transition from partial release of the valve to complete release of the valve.

In another preferred embodiment, there is provided a side delivered transcatheter heart valve with wire cells compressible along a vertical axis, wherein the annular support frame forms a two part framework, a first part comprises a flared atrial cuff joined to a second part that comprises a trans-annular tubular or cylindrical segment, wherein the cuff is joined to the trans-annular tubular or cylindrical segment around the circumference of a top edge of the trans-annular tubular or cylindrical segment.

BRIEF DESCRIPTION OF THE SEVERAL VIEWS OF DRAWING

FIG. 6 is an illustration of a SIDE VIEW of a compressed valve within a delivery catheter.

FIG. 7 is an illustration of a SIDE VIEW of a partially compressed valve, that is partially released from the delivery catheter and shows how blood flow can being its transition.

FIG. 8 is an illustration of a SIDE VIEW of a partially compressed valve showing blood flow through the valve and around the valve.

FIG. 9 is an illustration of a SIDE VIEW of an uncompressed valve orthogonally released (sideways) from the delivery catheter, and still attached to the distal pull wire/deployment control wire or hypotube releasably attached to the RVOT tab.

FIG. 10 is an illustration of a SIDE VIEW of an uncompressed valve showing transition to all blood flow through the valve and no flow around the valve.

Figure 25:
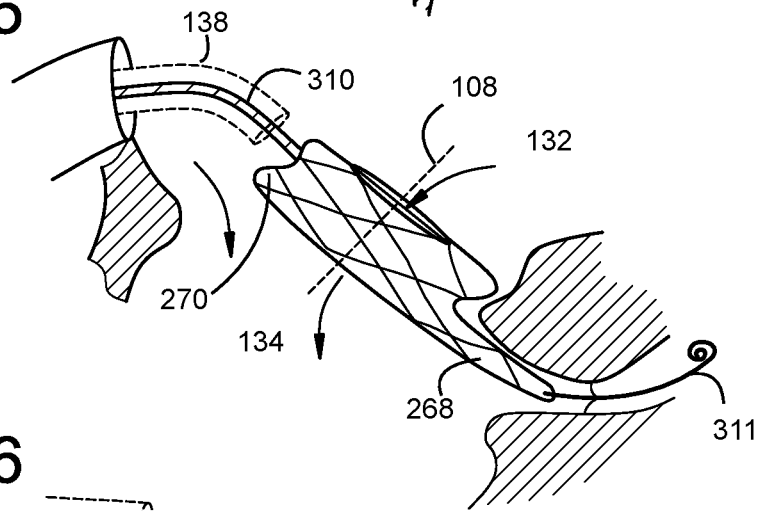

FIG. 25 is an illustration of a SIDE PERSPECTIVE view of a fully expelled or released valve that is lodged against the distal surface of the annulus and held elevated at an angle above the native annulus prior to complete deployment, and that allows a further transition from native blood flow through the native tricuspid valve with a partial flow around the prosthetic valve and into the native annulus, and an increasing partial flow thru the prosthetic valve into the native annulus.

Figure 26:
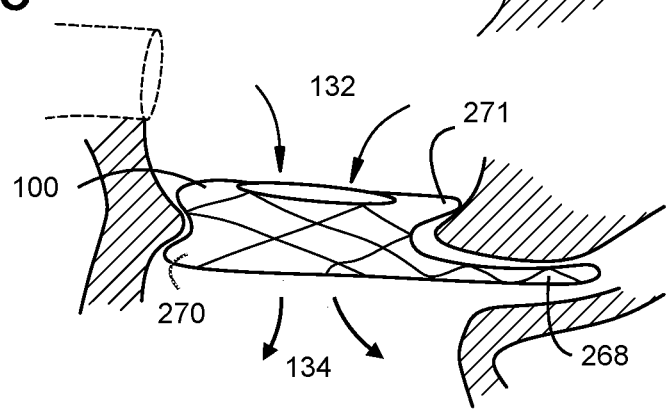

FIG. 26 is an illustration of a SIDE PERSPECTIVE view of a fully expelled or released valve that is completely seated into the native annulus, and that allows a smooth transition from native blood flow to a full, complete flow thru the prosthetic valve into the native annulus.

Figure 27:
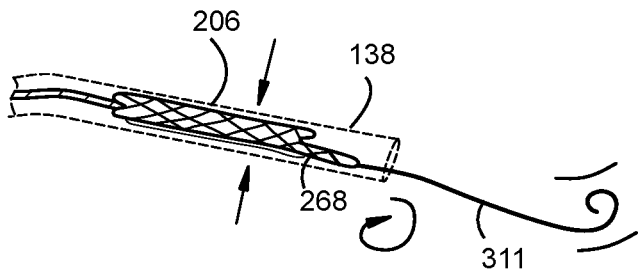

FIG. 27 is an illustration of a SIDE PERSPECTIVE view of a valve that is vertically compressed without folding and loaded into a delivery catheter, and shows an extended inner leaflet component in a rolled configuration.

Figure 28:
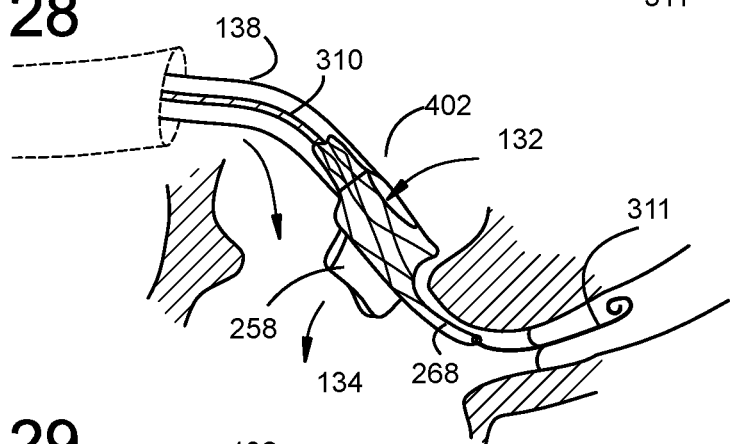

FIG. 28 is an illustration of a SIDE PERSPECTIVE view of a partially expelled or released valve, with a partially unfurled extended inner leaflet component, and shows a transition from native blood flow through the native tricuspid valve to a partial flow around the prosthetic valve and into the native annulus and a partial flow thru the prosthetic valve into the native annulus.

Figure 29:
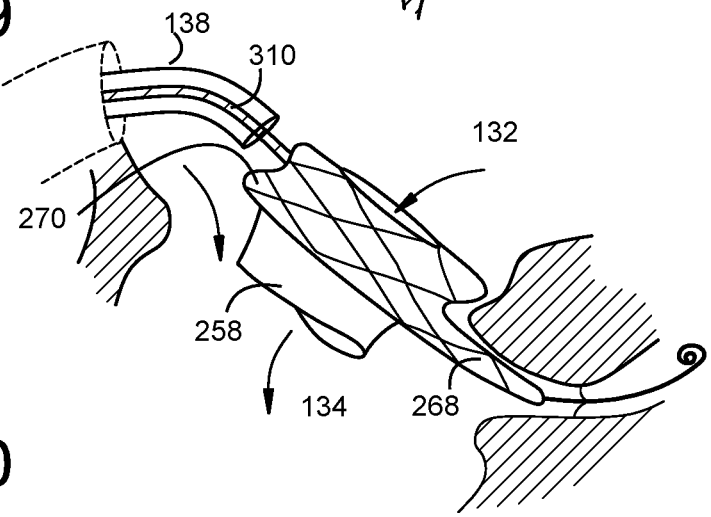

FIG. 29 is an illustration of a SIDE PERSPECTIVE view of a fully expelled or released valve, with a fully unfurled extended inner leaflet component, where the valve is lodged against the distal surface of the annulus and held elevated at an angle above the native annulus prior to complete deployment, and that allows a further transition from native blood flow through the native tricuspid valve with a partial flow around the prosthetic valve and into the native annulus, and an increasing partial flow thru the prosthetic valve into the native annulus.

Figure 30:
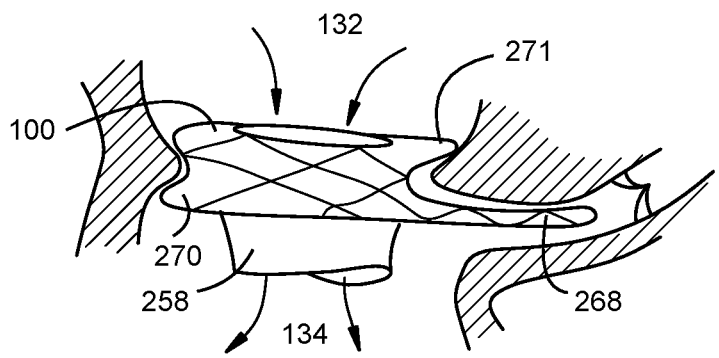

FIG. 30 is an illustration of a SIDE PERSPECTIVE view of a fully expelled or released valve, with a fully unfurled extended inner leaflet component, and shows that is completely seated into the native annulus, and that allows a smooth transition from native blood flow to a full, complete flow thru the prosthetic valve into the native annulus.

Figure 31:
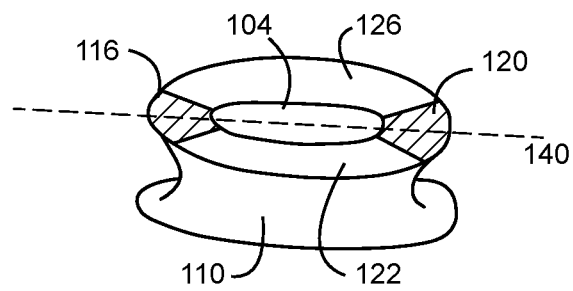

FIG. 31 is an illustration of a SIDE PERSPECTIVE view of a valve having a circular hyperboloid (hourglass) shape.

Figure 32:
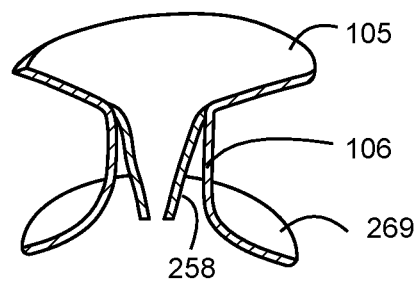

FIG. 32 is an illustration of a CUT-AWAY view of a valve having a circular hyperboloid (hourglass) shape.

Figure 33:
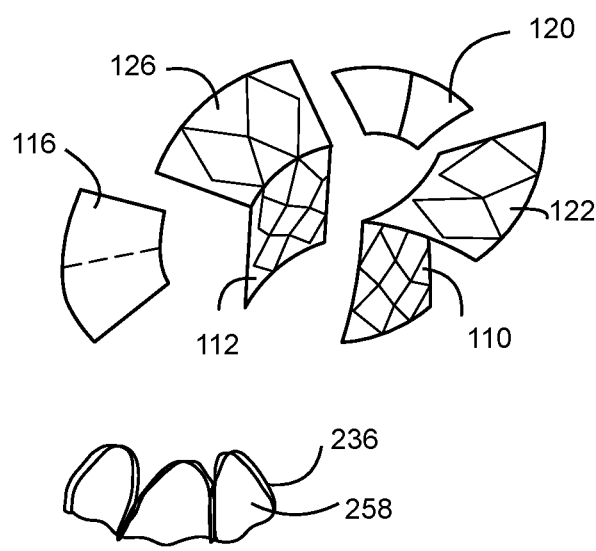

FIG. 33 is an illustration of an EXPLODED view of a valve having a funnel collar and cylinder body shape.

Figure 34:
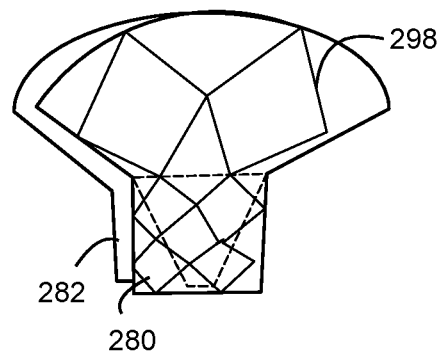

FIG. 34 is an illustration of a SIDE view of a two (2) panel embodiment of the valve.

Figure 35:
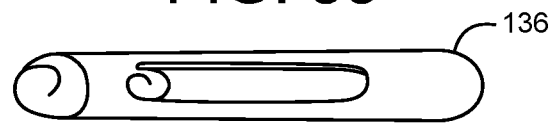

FIG. 35 is an illustration of a SIDE view of a roll-compressed two-panel embodiment of the valve.

Figure 36:
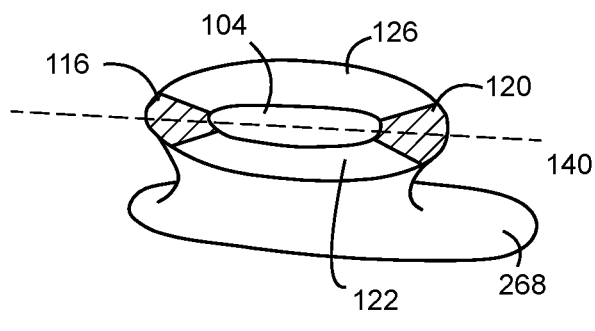

FIG. 36 is an illustration of a SIDE PERSPECTIVE view of a valve having a circular hyperboloid (hourglass) shape and an RVOT tab.

Figure 37:
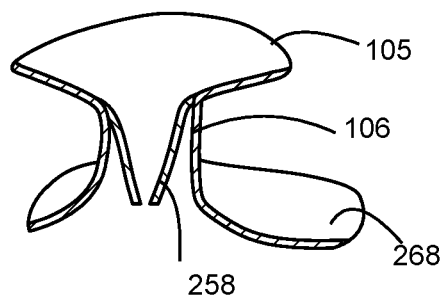

FIG. 37 is an illustration of a CUT-AWAY view of a valve having a circular hyperboloid (hourglass) shape and RVOT tab.

Figure 38:
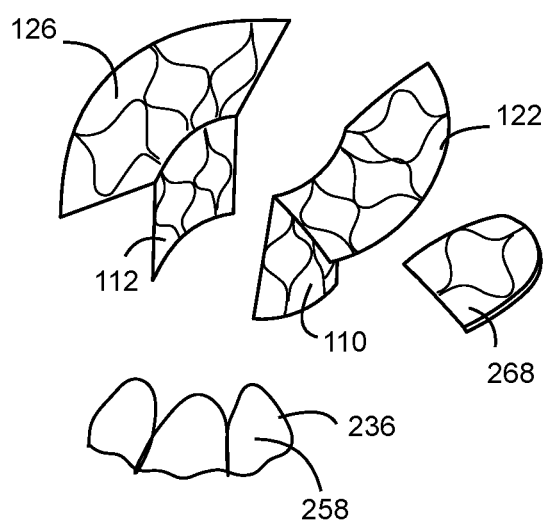

FIG. 38 is an illustration of an EXPLODED view of a valve having a funnel collar, cylinder body shape, and RVOT tab.

Figure 39:
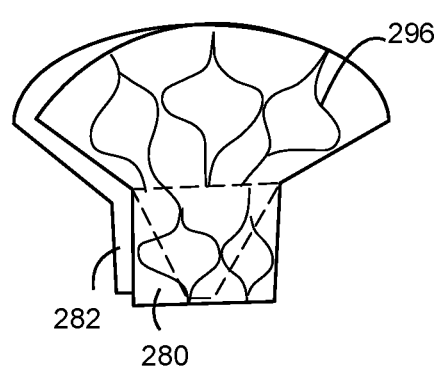

FIG. 39 is an illustration of a SIDE view of a two (2) panel embodiment of the valve with a panel RVOT tab.

Figure 40:
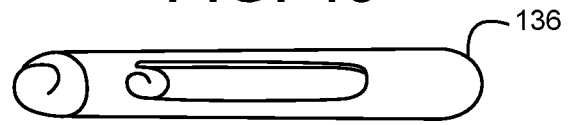

FIG. 40 is an illustration of a SIDE view of a roll-compressed two-panel embodiment of the valve with RVOT tab.

Figure 41:
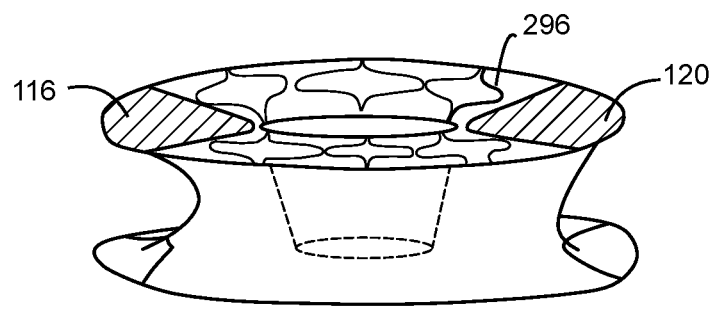

FIG. 41 is an illustration of a SIDE PERSPECTIVE view of a valve with a folding gap in the wire frame.

Figure 42:
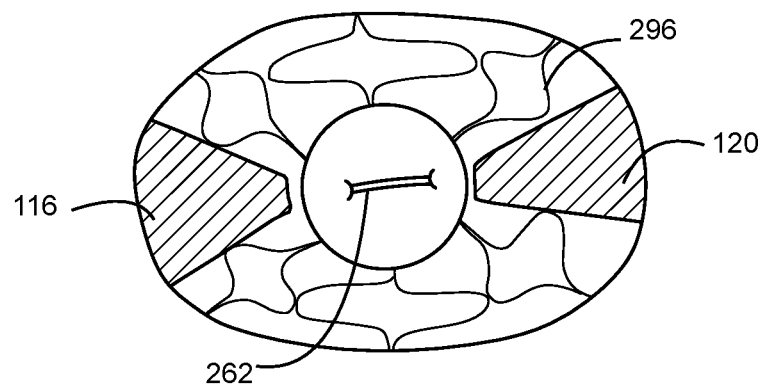

FIG. 42 is an illustration of a TOP view of a valve with a folding gap in the wire frame.

Figure 43:
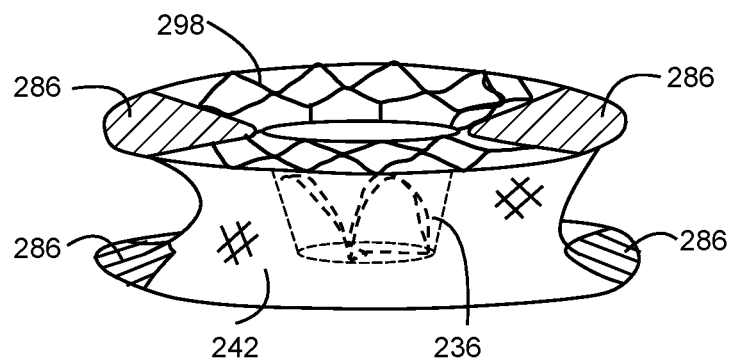

FIG. 43 is an illustration of a SIDE PERSPECTIVE view of a valve with a folding gap in a generic annular support wire frame.

Figure 44:
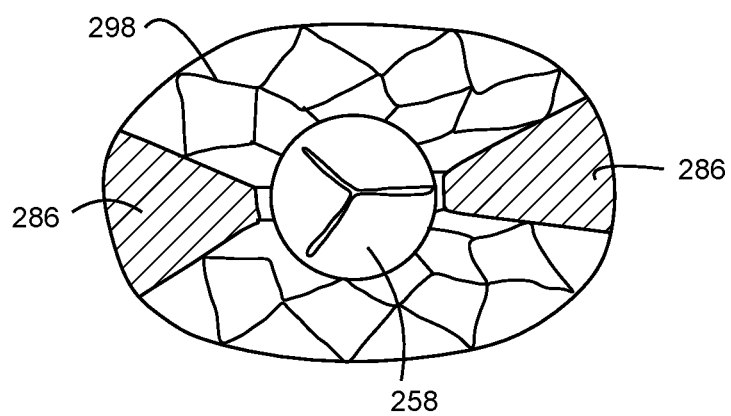

FIG. 44 is an illustration of a TOP view of a valve with a folding gap in the generic annular support wire frame.

Figure 45:
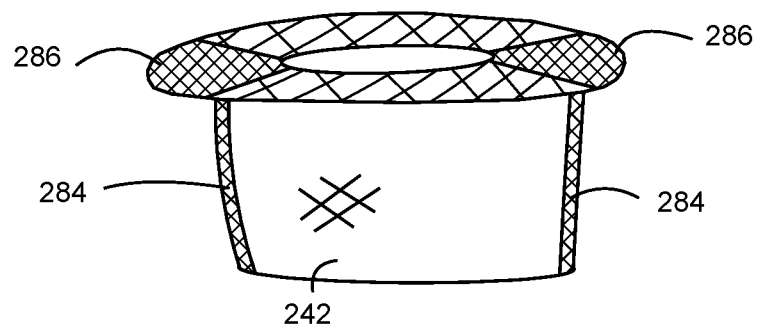

FIG. 45 is an illustration of a SIDE PERSPECTIVE view of a valve with a folding gap in the wire frame where the gap is covered with a fabric mesh spanning the gap, and also fabric folding panels on the proximal and distal sides of the lower body portion.

Figure 46:
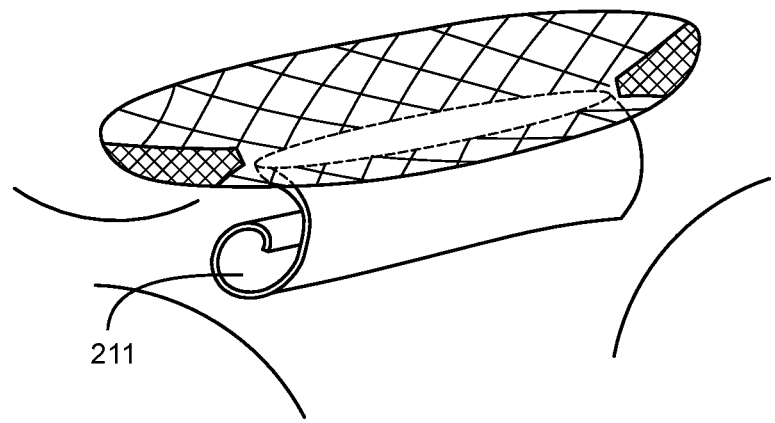

FIG. 46 is an illustration of a SIDE view of a partially rolled valve frame/sheet.

Figure 47:
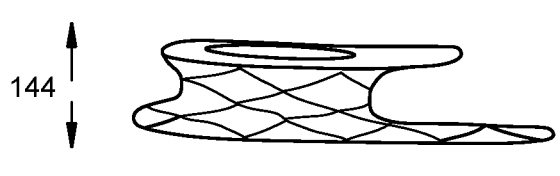

FIG. 47 is an illustration of a SIDE view of a vertically compressible valve with internal non-extending leaflets and compressible (wide) cells, in an expanded configuration.

Figure 48:
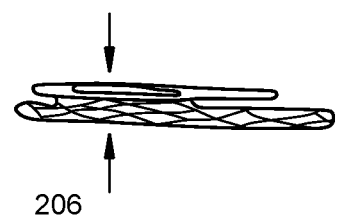

FIG. 48 is an illustration of a SIDE view of a vertically compressible valve with internal non-extending leaflets and compressible (wide) cells, in a compressed configuration.

Figure 49:
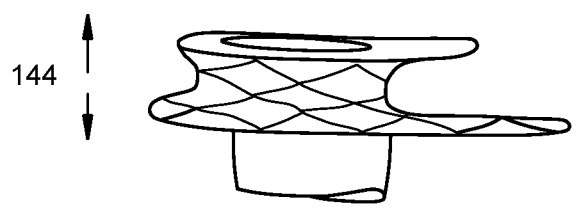

FIG. 49 is an illustration of a SIDE view of a vertically compressible valve with extended leaflets and compressible (wide) cells, in an expanded configuration.

Figure 50:
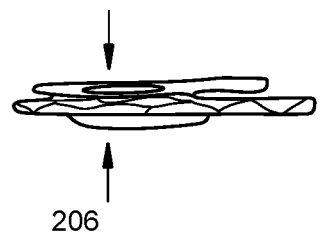

FIG. 50 is an illustration of a SIDE view of a vertically compressible valve with extended leaflets and compressible (wide) cells, in a compressed configuration where the wire frame is reduced in height and the extended leaflets are rolled up.

Figure 51:
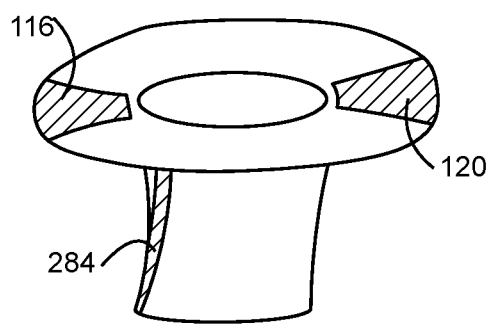

FIG. 51 is an illustration of a SIDE PERSPECTIVE view of valve having a flat collar and cylinder body.

Figure 52:
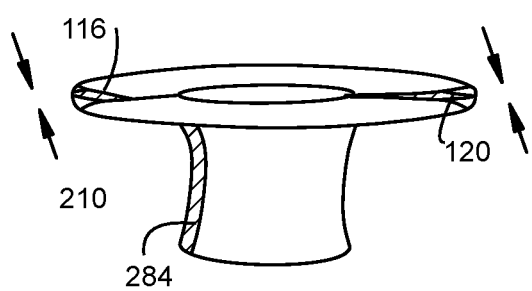

FIG. 52 is an illustration of a SIDE PERSPECTIVE view of the flattened, partially compressed valve.

Figure 53:
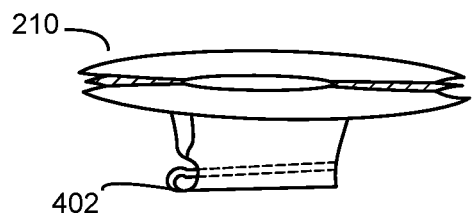

FIG. 53 is an illustration of a SIDE PERSPECTIVE view of the flattened, partially compressed valve with the lower body portion being compressed by rolling.

Figure 54:
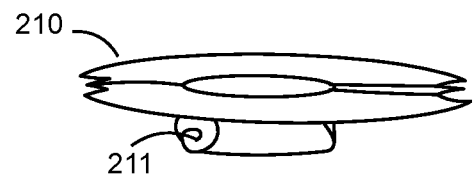

FIG. 54 is an illustration of a SIDE PERSPECTIVE view of the flattened, partially compressed valve with the lower body portion being completely compressed by rolling up to the collar portion.

Figure 55:

FIG. 55 is an illustration of a SIDE PERSPECTIVE view of the flattened, compressed valve with the lower body portion compressed by rolling and folded onto the flattened upper collar.

Figure 56:
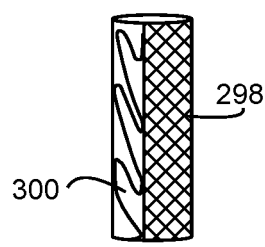

FIG. 56 is an illustration of a SIDE PERSPECTIVE view of a composite laser-cut workpiece prior to expansion into the valve frame.

Figure 57:
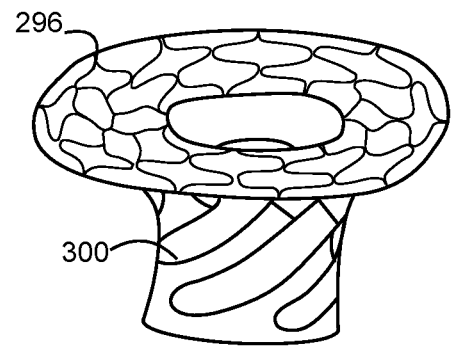

FIG. 57 is an illustration of a SIDE PERSPECTIVE view of the composite laser-cut workpiece after expansion into a valve wireframe.

Figure 58:
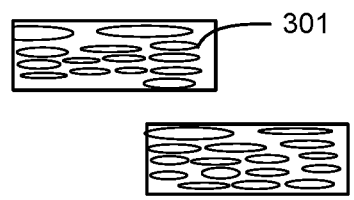

FIG. 58 is an illustration of a SIDE PERSPECTIVE view of laser-cut cell workpieces prior to expansion into the valve frame panels.

Figure 59:
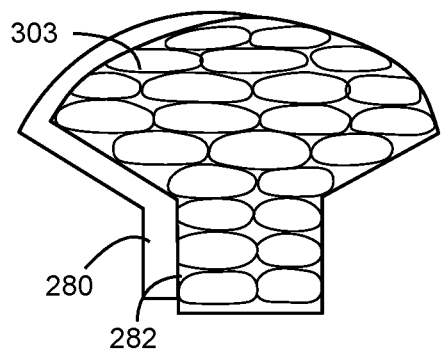

FIG. 59 is an illustration of a SIDE PERSPECTIVE view of the laser-cut workpieces after expansion into the valve wireframe panels.

Figure 60:
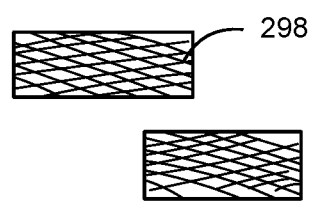

FIG. 60 is an illustration of a SIDE PERSPECTIVE view of laser-cut cell workpieces prior to expansion into the valve frame panels.

Figure 61:
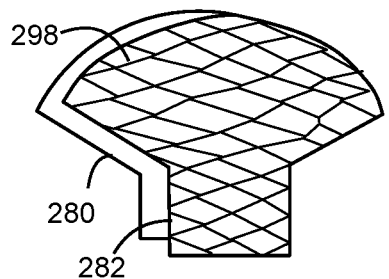

FIG. 61 is an illustration of a SIDE PERSPECTIVE view of the laser-cut workpieces after expansion into the valve wireframe panels.

Figure 62:
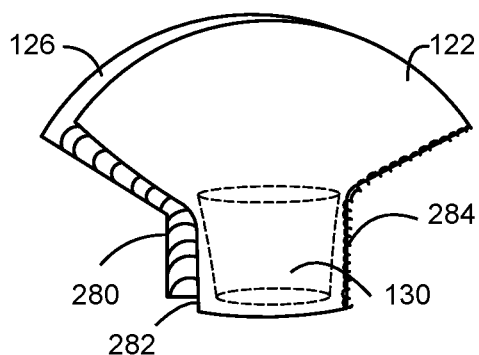

FIG. 62 is an illustration of a SIDE PERSPECTIVE view of valve wireframe panels that are stitched along the side edges to form a three-dimensional valve having an arc-shape collar and a cylinder body with an internal flow control component mounted within the body portion.

Figure 63:
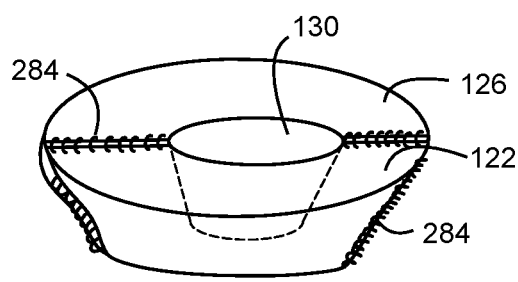

FIG. 63 is an illustration of a TOP PERSPECTIVE view of valve wireframe panels that are stitched along the side edges to form a three-dimensional valve having an arc-shape collar and a cylinder body with an internal flow control component mounted within the body portion.

Figure 64:
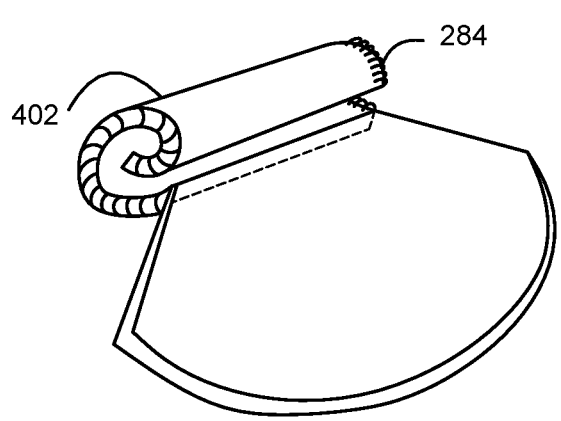

FIG. 64 is an illustration of a SIDE PERSPECTIVE view of the two-panel embodiment being compressed by rolling.

Figure 65:
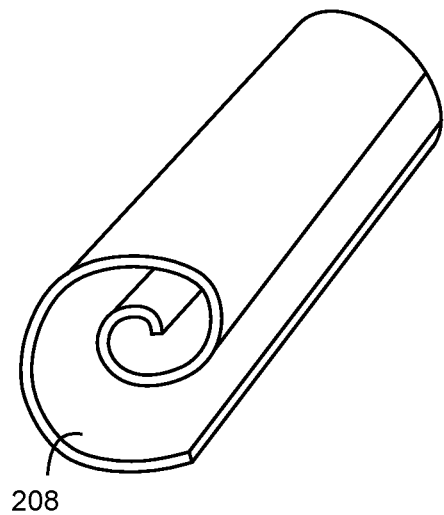

FIG. 65 is an illustration of a SIDE PERSPECTIVE view of a two-panel embodiment rolled at least 1 turn, and up to 1.5 turns, or at least 360 degrees, and up to at least 540 degrees.

Figure 66:
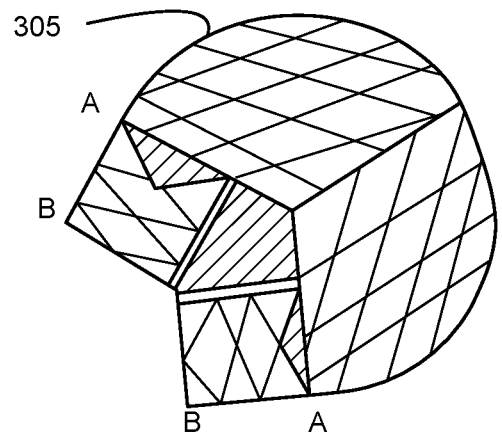

FIG. 66 is an illustration of a TOP view of a single sheet of metal or metal alloy with compressible cells cut or formed into a first and second collar panel and a first and second body portion.

Figure 67:
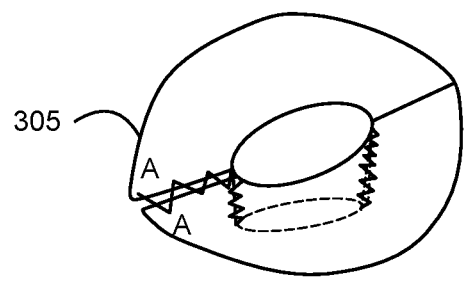

FIG. 67 is an illustration of a TOP PERSPECTIVE view of the single sheet valve frame after folding, assembly, and attachment along the open seams.

Figure 68:
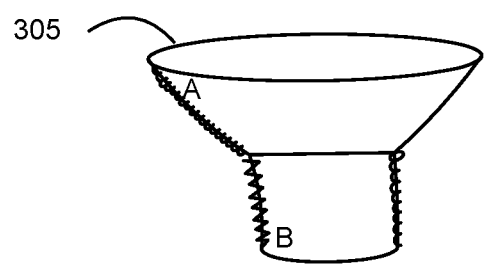

FIG. 68 is an illustration of a SIDE PERSPECTIVE view of the single sheet valve frame after folding, assembly, and attachment along the open seams.

Figure 69:
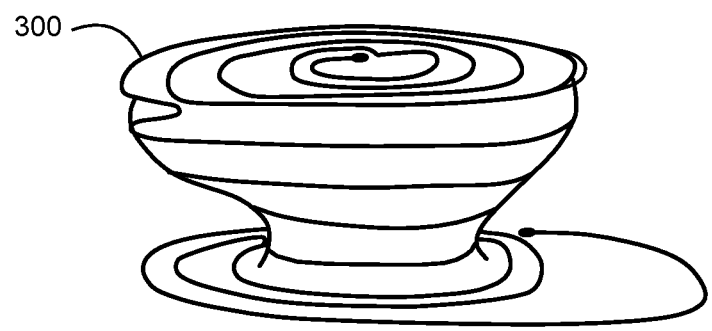

FIG. 69 is an illustration of a SIDE PERSPECTIVE view of a valve formed from a single continuous wire, with an upper collar portion, an hourglass shape for the body portion, and an RVOT tab extending away from the lower edge of the body portion.

Figure 70:
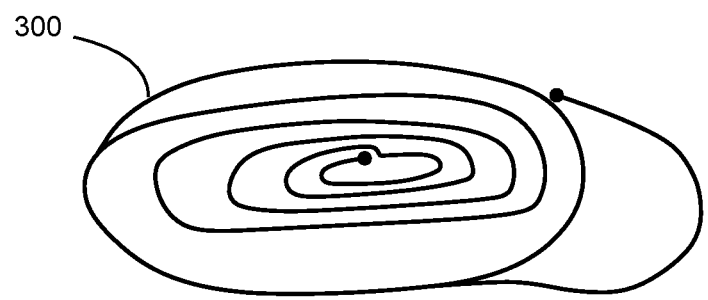

FIG. 70 is an illustration of a TOP view of a valve formed from a single continuous wire, with an upper collar portion, an hourglass shape for the body portion (not shown), and an RVOT tab extending away from the lower edge of the body portion.

Figure 71:
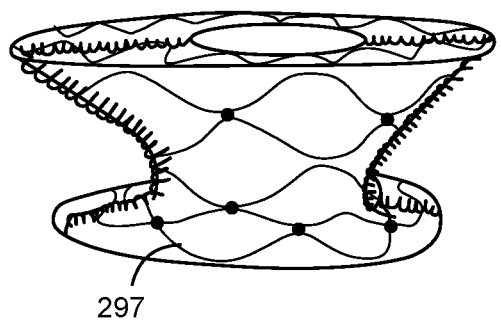

FIG. 71 is an illustration of a SIDE PERSPECTIVE view of a valve formed from a series of wave-shaped wires connected at connection points, with an upper collar portion, and an hourglass shape for the body portion.

Figure 72:
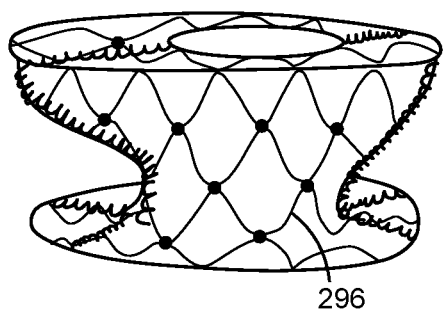

FIG. 72 is an illustration of a SIDE PERSPECTIVE view of a valve formed from a series of zigzag-shaped wires connected at connection points, with an upper collar portion, and an hourglass shape for the body portion.

Figure 73:
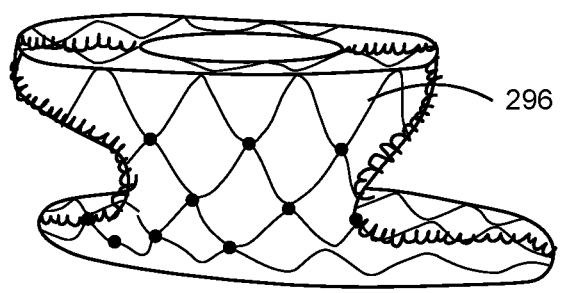

FIG. 73 is an illustration of a SIDE PERSPECTIVE view of a valve formed from a series of wave-shaped wires connected at connection points, with an upper collar portion, an hourglass shape for the body portion, and an RVOT tab extending away from the lower edge of the body portion.

Figure 74:
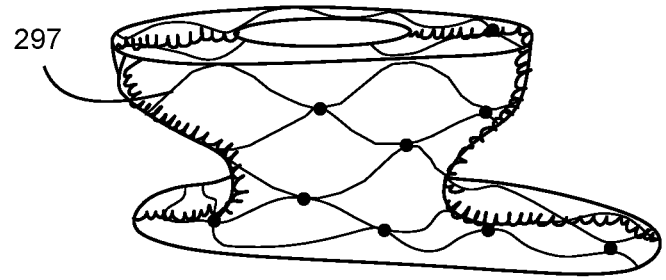

FIG. 74 is an illustration of a SIDE PERSPECTIVE view of a valve formed from a series of zigzag-shaped wires connected at connection points, with an upper collar portion, an hourglass shape for the body portion, and an RVOT tab extending away from the lower edge of the body portion.

Figure 75:
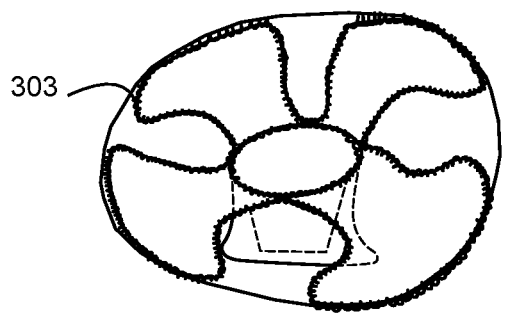

FIG. 75 is an illustration of a TOP PERSPECTIVE view of a valve upper collar portion formed from a series of fan-shaped wires connected circumferentially to the top peripheral edge of the lower body portion.

Figure 76:
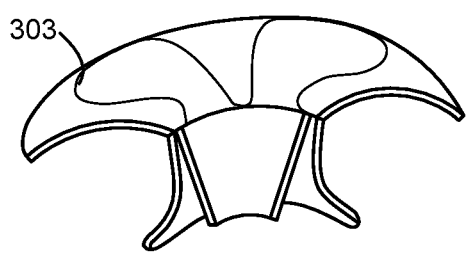
Figure 77:
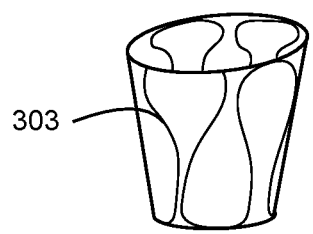

FIG. 76 is an illustration of a CUT-AWAY view of a valve upper collar portion formed from a series of fan-shaped wires connected circumferentially to the top peripheral edge of the lower body portion, and shows half of the flow control component mounted with the lower body portion FIG. 77 is an illustration of a SIDE PERSPECTIVE view of an upper cuff or collar in a partially expanded configuration, showing how the elongated fan-shape wires permit elongation and radial compression.

Figure 78:
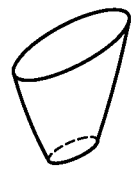

FIG. 78 is an illustration of a SIDE PERSPECTIVE view of a two-panel embodiment of a flow control component.

Figure 79:
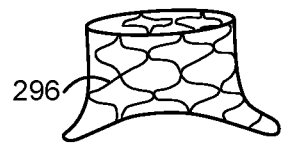

FIG. 79 is an illustration of a SIDE PERSPECTIVE view of a lower body portion having a braided wire cell construction.

Figure 80:
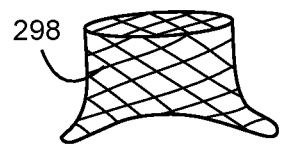

FIG. 80 is an illustration of a SIDE PERSPECTIVE view of a lower body portion having a laser-cut wire cell construction.

Figure 81:
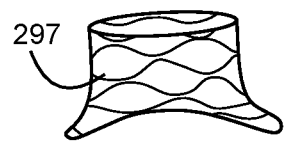

FIG. 81 is an illustration of a SIDE PERSPECTIVE view of a lower body portion having a connected-wave wire cell construction.

Figure 82:
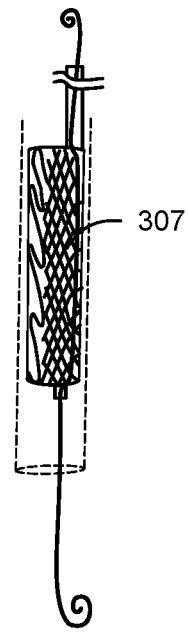

FIG. 82 is an illustration of a SIDE view of a compressed valve within a delivery catheter, and shows draw/pulling wire attached to the forward end of the compressed valve to pull the valve out of the catheter.

Figure 83:
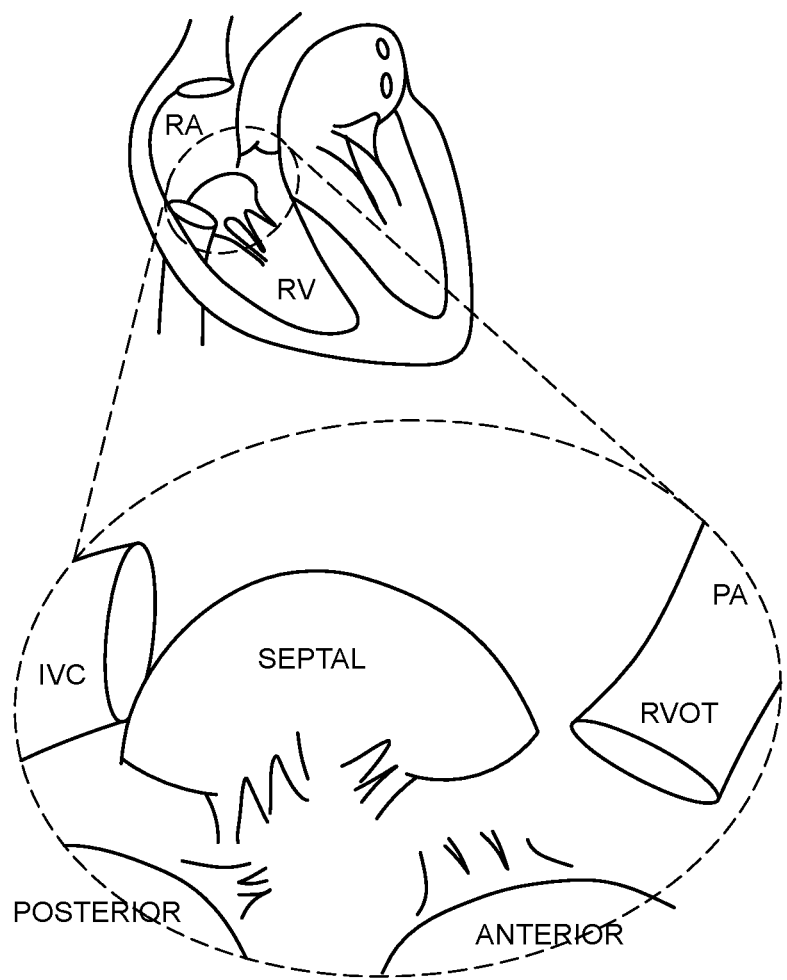

FIG. 83 is an illustration of a SIDE view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

Figure 84:
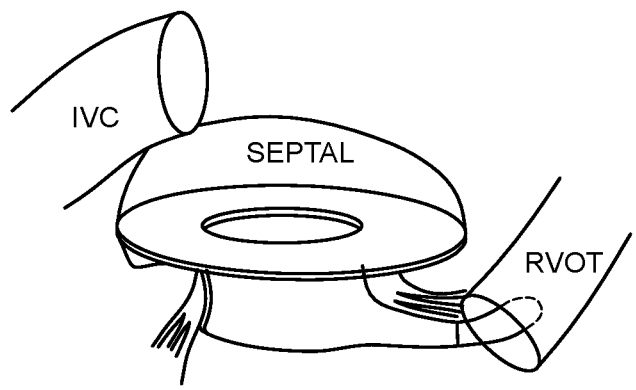

FIG. 84 is an illustration of a SIDE PERSPECTIVE view of a side delivered valve seated with the native tricuspid annulus with collar portion laying atrially above the tricuspid annulus and leaflets, lower body portion extending into and through the annulus to provide corrective hemodynamic flow from the flow control component, and RVOT footer tab and RVOT/PA extender wire.

Figure 85:
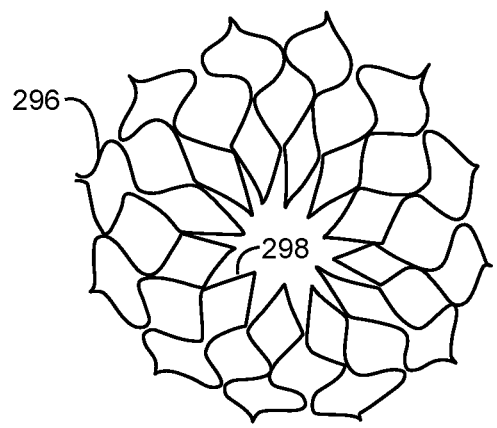

FIG. 85 is an illustration of a TOP view of flat wire frame of metal or metal alloy having compressible wire cells configured in a strain minimizing orientation to facilitate loading and delivery of a prosthetic tricuspid valve.

Figure 86:
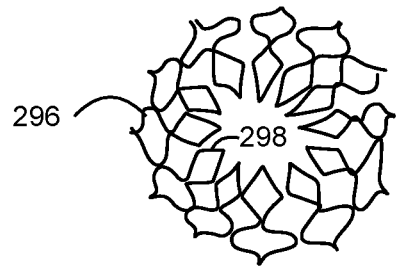

FIG. 86 is an illustration of a TOP view of smaller sized flat wire frame of metal or metal alloy having compressible wire cells configured in a strain minimizing orientation to facilitate loading and delivery of a prosthetic tricuspid valve.

Figure 87:
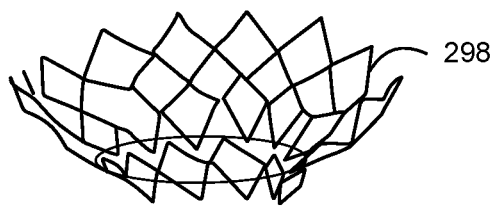

FIG. 87 is an illustration of a SIDE PERSPECTIVE view of a wire frame in a funnel configuration (heat set) showing compressible wire cells configured in a strain minimizing orientation to facilitate loading and delivery of a prosthetic tricuspid valve.

Figure 88:
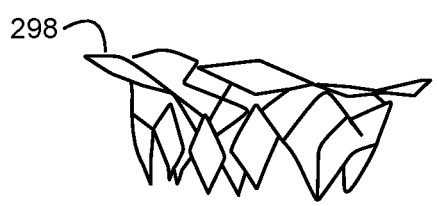

FIG. 88 is an illustration of a SIDE PERSPECTIVE view of a wire frame in a funnel configuration (heat set) showing compressible wire cells configured in a strain minimizing orientation to facilitate loading and delivery of a prosthetic tricuspid valve.

Figure 89:
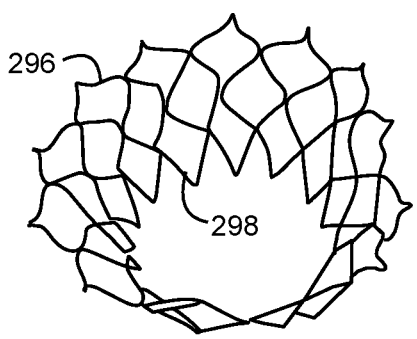

FIG. 89 is an illustration of a TOP view down the central axis of a wire frame in a funnel configuration (heat set) showing compressible wire cells configured in a strain minimizing orientation to facilitate loading and delivery of a prosthetic tricuspid valve.

Figure 90:
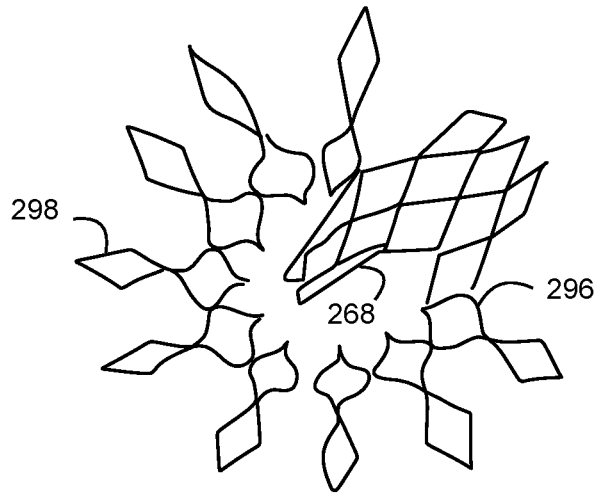

FIG. 90 is an illustration of a TOP view of flat wire frame having an RVOT tab of metal or metal alloy having compressible wire cells configured in a strain minimizing orientation to facilitate orthogonal loading and delivery of a prosthetic tricuspid valve.

Figure 91:
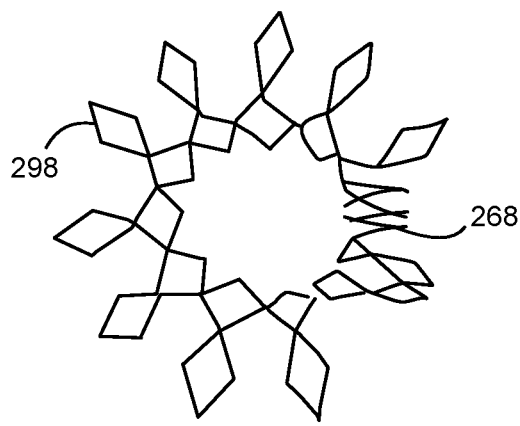

FIG. 91 is an illustration of a TOP view of a wire frame with RVOT tab in a funnel configuration (heat set) showing compressible wire cells configured in a strain minimizing orientation to facilitate orthogonal loading and delivery of a prosthetic tricuspid valve.

Figure 92:
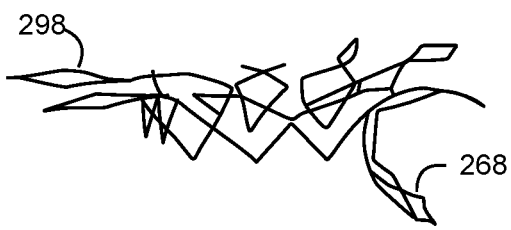

FIG. 92 is an illustration of a SIDE view of a wire frame with RVOT tab in a funnel configuration (heat set) showing compressible wire cells configured in a strain minimizing orientation to facilitate orthogonal loading and delivery of a prosthetic tricuspid valve.

Figure 93:
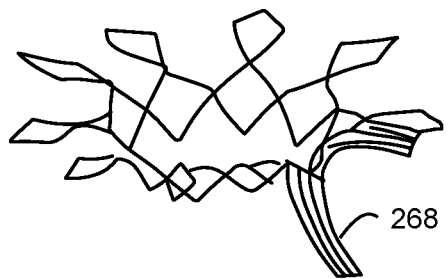

FIG. 93 is an illustration of a SIDE PERSPECTIVE view of a wire frame with RVOT tab in a funnel configuration (heat set) showing compressible wire cells configured in a strain minimizing orientation to facilitate orthogonal loading and delivery of a prosthetic tricuspid valve.

Figure 94:
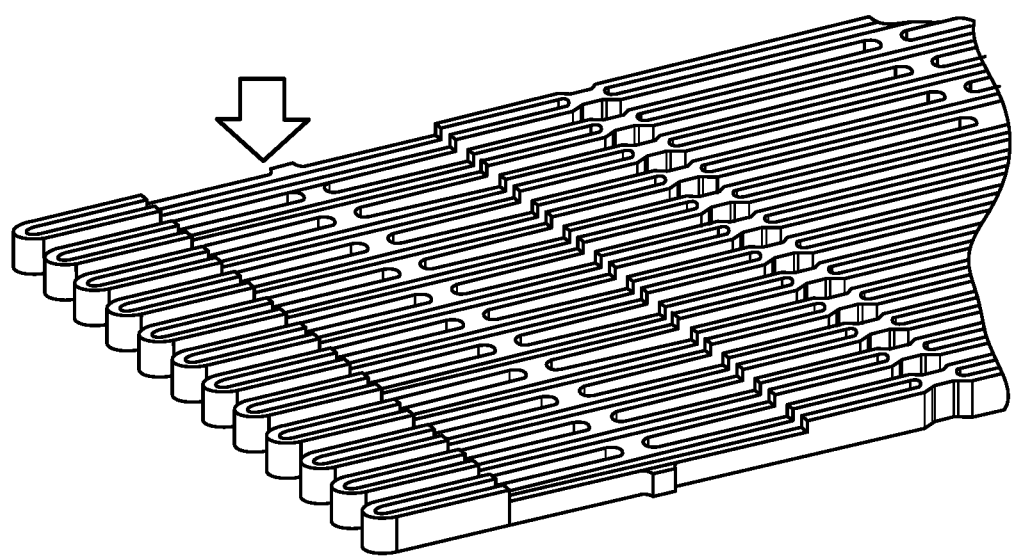

FIG. 94 is an illustration of a SIDE PERSPECTIVE view of a metal alloy sheet that has been etched partially on a single side using photolithography and resistive masks.

Figure 95:
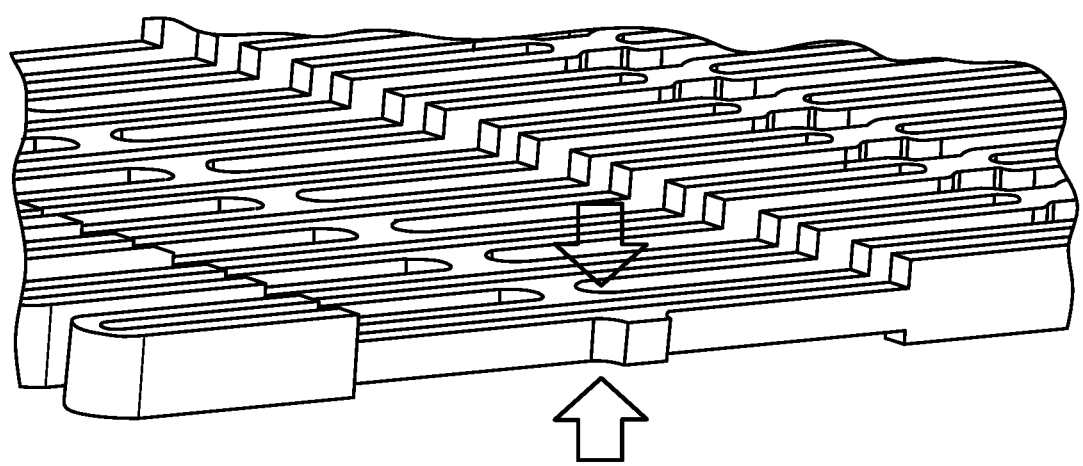

FIG. 95 is an illustration of a SIDE PERSPECTIVE view of a metal alloy sheet that has been etched partially in a two-sided configuration using photolithography and resistive masks.

DETAILED DESCRIPTION OF THE INVENTION

The invention is directed to a transcatheter heart valve replacement that is a low profile, side delivered implantable prosthetic heart valve having a ring-shaped or annular support frame, an inner 2- or 3-panel sleeve, an elongated sub-annular tension arm extending into the right ventricular outflow tract, and one or more anchor elements.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Definitions

Side-Delivery or Orthogonal Delivery

In the description and claims herein, the terms "side-delivered", "side-delivery", "orthogonal", "orthogonally delivered" and so forth are used to describe that the valves of the present invention are compressed and delivered at a roughly 90 degree angle compared to traditional transcatheter heart valves. Orthogonal delivery is a transverse delivery where a perimeter distal sidewall exits the delivery catheter first, followed by the central aperture, followed by the proximal sidewall.

Traditional valves have a central cylinder axis that is parallel to the length-wise axis of the delivery catheter and are deployed from the end of the delivery catheter and expanded radially outward from the central annular axis, in a manner akin to pushing a closed spring-loaded umbrella out of a sleeve to make it spring open. However, the valves of the present invention are compressed and delivered in a sideways manner. To begin with the shape of the expanded valve is that of a large diameter shortened cylinder with an extended collar or cuff. The valves are compressed, in one preferred embodiment, where the central axis of the valve is roughly perpendicular to (orthogonal to) the length-wise axis of the delivery catheter. In one preferred embodiment, the valves are compressed vertically, similar to collapsing the height of a cylinder accordion-style from taller to shorter, and the valves are also compressed by folding a front panel against a back panel. In another preferred embodiment, the valves may be compressed by rolling.

Traditional valves can only be expanded as large as what the internal diameter of the delivery catheter will allow. Efforts to increase the expanded diameter of traditional valves have run into the problems of trying to compress too much material and structure into too little space.

Mathematically, the term orthogonal refers to an intersecting angle of 90 degrees between two lines or planes. As used, herein the term "substantially orthogonal" refers to an intersecting angle ranging from 75 to 105 degrees. The intersecting angle or orthogonal angle refers to both (i) the relationship between the length-wise cylindrical axis of the delivery catheter and the long-axis of the compressed valve of the invention, where the long-axis is perpendicular to the central cylinder axis of traditional valves, and (ii) the relationship between the long-axis of the compressed or expanded valve of the invention and the axis defined by the blood flow through the prosthetic heart valve where the blood is flowing, e.g. from one part of the body or chamber of the heart to another downstream part of the body or chamber of the heart, such as from an atrium to a ventricle through a native annulus.

Transcatheter

In the description and claims herein, the term "transcatheter" is used to define the process of accessing, controlling, and delivering a medical device or instrument within the lumen of a catheter that is deployed into a heart chamber, as well as an item that has been delivered or controlled by such as process. Transcatheter access is known to include via femoral artery and femoral vein, via brachial artery and vein, via carotid and jugular, via intercostal (rib) space, and via sub-xyphoid. Transcatheter can be synonymous with transluminal and is functionally related to the term "percutaneous" as it relates to delivery of heart valves.

In preferred embodiments of the invention, the transcatheter approach includes (i) advancing to the tricuspid valve or pulmonary artery of the heart through the inferior vena cava via the femoral vein, (ii) advancing to the tricuspid valve or pulmonary artery of the heart through the superior vena cava via the jugular vein, (iii) advancing to the mitral valve of the heart through a trans-atrial approach, e.g. fossa ovalis or lower, via the IVC-femoral or the SVC-jugular approach.

Annular Support Frame

In the description and claims herein, the term "annular support frame", and also "wire frame" or "flange or "collar" refers to a three-dimensional structural component that is seated within a native valve annulus and is used as a mounting element for a leaflet structure, a flow control component, or a flexible reciprocating sleeve or sleeve-valve.

In a preferred embodiment, the annular support frame is a self-expanding annular support frame, having a central channel and an outer perimeter wall circumscribing a central vertical axis in an expanded configuration. The perimeter wall encompasses both the collar and the lower body portions.

The perimeter wall can be further defined as having a front wall portion and a back wall portion, which are connected along a near side (to the IVC) or proximal side to a proximal fold area, and connected along a far or distal side to a distal fold area.

This front wall portion can be further defined as having a front upper collar portion and a front lower body portion, and the back wall portion can be further defined as having a back upper collar portion and a back lower body portion.

The annular support frame has a flow control component mounted within the annular support frame and configured to permit blood flow in a first direction through an inflow end of the valve and block blood flow in a second direction, opposite the first direction, through an outflow end of the valve.

Since the frame is preferably made of superelastic metal or alloy such as Nitinol, the frame is compressible. Preferably, the frame is constructed of a plurality of compressible wire cells having an orientation and cell geometry substantially orthogonal to the central vertical axis to minimize wire cell strain when the annular support frame when configured in a vertical compressed configuration, a rolled compressed configuration, or a folded compressed configuration.

Annular Support Frame Structure

The annular support frame can be a ring, or cylindrical or conical tube, made from a durable, biocompatible structural material such as Nitinol or similar alloy, wherein the annular support frame is formed by manufacturing the structural material as a braided wire frame, a laser-cut wire frame, or a wire loop. The annular support frame is about 5-60 mm in height, has an outer diameter dimension, R, of 30-80 mm, and an inner diameter dimension of 31-79 mm, accounting for the thickness of the wire material itself. As stated, the annular support frame can have a side-profile of a ring shape, cylinder shape, conical tube shape, but may also have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both.

In one preferred embodiment, the annular support frame used in the prosthetic heart valve deployed in the tricuspid annulus may have a complex shape determined by the anatomical structures where the valve is being mounted. For example, in the tricuspid annulus, the circumference of the tricuspid valve may be a rounded ellipse, the septal wall is known to be substantially vertical, and the tricuspid is known to enlarge in disease states along the anterior-posterior line. Accordingly, a prosthetic heart valve may start in a roughly tubular configuration, and be heat-shaped to provide an upper atrial cuff or flange for atrial sealing and a lower trans-annular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment.

In a preferred embodiment, the horizontal x-axis of the valve is orthogonal to (90 degrees), or substantially orthogonal to (75-105 degrees), or substantially oblique to (45-135 degrees) to the central vertical y-axis when in an expanded configuration.

In a preferred embodiment, the horizontal x-axis of the compressed configuration of the valve is substantially parallel to a length-wise cylindrical axis of the delivery catheter.

In another preferred embodiment, the valve has a compressed height (y-axis) and width (z-axis) of 6-15 mm, preferably 8-12 mm, and more preferably 9-10 mm, and an expanded deployed height of about 5-60 mm, preferably about 5-30 mm, and more preferably about 5-20 mm or even 8-12 mm or 8-10 mm. It is contemplated in preferred embodiments that the length of the valve, x-axis, does not require compression since it can extend along the length of the central cylindrical axis of the delivery catheter.

In a preferred embodiment, the valve has an expanded diameter length and width of 25-80 mm, preferably 40-80 mm, and in certain embodiments length and/or width may vary and include lengths of 25 mm, 30 mm, 35 mm, 40 mm, 45 mm, 50 mm, 55 mm, 60 mm, 65 mm, 70 mm, 75 mm, and 80 mm, in combination with widths that are the same or different as the length.

In certain preferred embodiments, the valve is centric, or radially symmetrical. In other preferred embodiments, the valve is eccentric, or radially (y-axis) asymmetrical. In some eccentric embodiments, the outer frame may have a D-shape (viewed from the top) so the flat portion can be matched to the mitral annulus near the anterior leaflet.

In certain preferred embodiments, the inner frame holding the leaflet tissue is 25-29 mm in diameter, the outer frame is 50-70 mm in diameter, and the collar structure extends beyond the top edge of the outer frame by 10-30 mm to provide a seal on the atrial floor against perivalvular leaks (PVLs).

The atrial collar is shaped to conform to the native deployment location. In a mitral replacement, the atrial collar will be configured with varying portions to conform to the native valve. In one preferred embodiment, the collar will have a distal and proximal upper collar portion. The distal collar portion can be larger than the proximal upper collar portion to account for annular or subannular geometries.

Annular Support Frame Covering

The annular support frame is optionally internally or externally covered, partially or completely, with a biocompatible material such as pericardium. The annular support frame may also be optionally externally covered, partially or completely, with a second biocompatible material such as polyester or Dacron®.

Annular Support Frame Purpose

The annular support frame has a central axial lumen where a prosthetic heart valve or flow-control structure, such as a reciprocating compressible sleeve, is mounted across the diameter of the lumen. The annular support frame is also tensioned against the inner aspect of the native annulus and provides structural patency to a weakened annular ring.

Annular Support Frame Optional Collars

The annular support frame may optionally have a separate atrial collar attached to the upper (atrial) edge of the frame, for deploying on the atrial floor, that is used to direct blood from the atrium into the sleeve and to seal against blood leakage around the annular support frame. The annular support frame may also optionally have a separate ventricular collar attached to the lower (ventricular) edge of the frame, for deploying in the ventricle immediately below the native annulus that is used to prevent regurgitant leakage during systole, to prevent dislodging of the device during systole, to sandwich or compress the native annulus or adjacent tissue against the atrial collar, and optionally to attach to and support the sleeve/conduit.

Annular Support Frame Delivery

The annular support frame may be compressed for transcatheter delivery and may be expandable as a self-expandable shape-memory element or using a transcatheter expansion balloon. Some embodiments may have both an atrial collar and a ventricular collar, whereas other embodiments within the scope of the invention include prosthetic heart valves having either a single atrial collar, a single ventricular collar, or having no additional collar structure.

Frame Material

Preferably, the frame is made from a superelastic metal component, such as laser-cut Nitinol tube, or flat sheet or other similarly functioning material such as braided wire. The material may be used for the frame/stent, for the collar, and/or for anchors. It is contemplated as within the scope of the invention to use other shape memory alloys, as well as polymer composites including composites containing carbon nanotubes, carbon fibers, metal fibers, glass fibers, and polymer fibers. It is contemplated that the frame may be constructed as a braid, wire, or laser cut frame. Laser cut frames are preferably made from Nitinol, but also without limitation made from stainless steel, cobalt chromium, titanium, and other functionally equivalent metals and alloys.

One key aspect of the frame design is that it be compressible and when released have the stated property that it returns to its original (uncompressed) shape. This requirement limits the potential material selections to metals and plastics that have shape memory properties. With regards to metals, Nitinol has been found to be especially useful since it can be processed to be austenitic, martensitic or super elastic. Martensitic and super elastic alloys can be processed to demonstrate the required mechanical behavior.

Laser Cut

One possible construction of the wire frame envisions the laser cutting of a thin, isodiametric Nitinol tube. The laser cuts form regular cutouts in the thin Nitinol tube. In one preferred embodiment, the Nitinol tube expands to form a three-dimensional structure formed from diamond-shaped cells. The structure may also have additional functional elements, e.g. loops, anchors, etc. for attaching accessory components such as biocompatible covers, tissue anchors, releasable deployment and retrieval control guides, knobs, attachments, rigging, and so forth.

Secondarily the tube is thermo-mechanically processed using industry standard Nitinol shape forming methods. The treatment of the wire frame in this manner will form a device that has shape memory properties and will readily revert to the memory shape once deployed.

Braided Wire

Another possible construction of the wire frame envisions utilizing simple braiding techniques using a Nitinol wire and a simple braiding fixture. The wire is wound on the braiding fixture in a pattern until an isodiametric tube is formed. Secondarily, the braided wire frame is placed on a shaping fixture and processed using industry standard Nitinol shape forming methods.

Flow Control Component

In the description and claims herein, the term "flow control component" refers in a non-limiting sense to a leaflet structure having 2-, 3-, 4-leaflets of flexible biocompatible material such a treated or untreated pericardium that is sewn or joined to an annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating".

Tissue Anchor

In the description and claims herein, the term "tissue anchor" or "plication tissue anchor" or "secondary tissue anchor", or "dart" or "pin" refers to a fastening device that connects the upper atrial frame to the native annular tissue, usually at or near the periphery of the collar. The anchor may be positioned to avoid piercing tissue and just rely on the compressive force of the two plate-like collars on the captured tissue, or the anchor, itself or with an integrated securement wire, may pierce through native tissue to provide anchoring, or a combination of both. The anchor may have a specialized securement mechanism, such as a pointed tip with a groove and flanged shoulder that is inserted or popped into a mated aperture or an array of mated apertures that allow the anchor to attach, but prevent detachment when the aperture periphery locks into the groove near the flanged shoulder. The securement wire may be attached or anchored to the collar opposite the pin by any attachment or anchoring mechanisms, including a knot, a suture, a wire crimp, a wire lock having a cam mechanism, or combinations.

Support Post

The term "support post" refers to a rigid or semi-rigid length of material such as Nitinol or PEEK, that may be mounted on a spoked frame and that runs axially, or down the center of, or within a sewn seam of the flexible sleeve. The sleeve may be unattached to the support post, or the sleeve may be directly or indirectly attached to the support post.

The term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a tricuspid or mitral valve replacement will be implanted at the tricuspid or mitral annulus. Certain features of the present invention are particularly advantageous for one implantation site or the other. However, unless the combination is structurally impossible, or excluded by claim language, any of the heart valve embodiments described herein could be implanted in any body channel.

The term "lumen" refers to the inside of the cylinder tube. The term "bore" refers to the inner diameter.

The term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Prosthetic Heart Valve

The term prosthesis or prosthetic encompasses both complete replacement of an anatomical part, e.g. a new mechanical valve replaces a native valve, as well as medical devices that take the place of and/or assist, repair, or improve existing anatomical parts, e.g. native valve is left in place. For mounting within a passive assist cage, the invention contemplates a wide variety of (bio)prosthetic artificial heart valves. Contemplated as within the scope of the invention are ball valves (e.g. Starr-Edwards), bileaflet valves (St. Jude), tilting disc valves (e.g. Bjork-Shiley), stented pericardium heart-valve prosthesis' (bovine, porcine, ovine) (Edwards line of bioprostheses, St. Jude prosthetic heart valves), as well as homograft and autograft valves. For bioprosthetic pericardial valves, it is contemplated to use bioprosthetic aortic valves, bioprosthetic mitral valves, bioprosthetic tricuspid valves, and bioprosthetic pulmonary valves.

Tethers

The tethers are made from surgical-grade materials such as biocompatible polymer suture material. Non-limiting examples of such material include ultra high-molecular weight polyethylene (UHMWPE), 2-0 exPFTE(polytetrafluoroethylene) or 2-0 polypropylene. In one embodiment the tethers are inelastic. It is also contemplated that one or more of the tethers may optionally be elastic to provide an even further degree of compliance of the valve during the cardiac cycle.

Tines—Anchors—Tines/Barbs

The device can be seated within the valvular annulus through the use of tines or barbs. These may be used in conjunction with, or in place of one or more tethers. The tines or barbs are located to provide attachment to adjacent tissue. Tines are forced into the annular tissue by mechanical means such as using a balloon catheter. In one non-limiting embodiment, the tines may optionally be semi-circular hooks that upon expansion of the wire frame body, pierce, rotate into, and hold annular tissue securely. Anchors are deployed by over-wire delivery of an anchor or anchors through a delivery catheter. The catheter may have multiple axial lumens for delivery of a variety of anchoring tools, including anchor setting tools, force application tools, hooks, snaring tools, cutting tools, radio-frequency and radiological visualization tools and markers, and suture/thread manipulation tools. Once the anchor(s) are attached to the moderator band, tensioning tools may be used to adjust the length of tethers that connect to an implanted valve to adjust and secure the implant as necessary for proper functioning. It is also contemplated that anchors may be spring-loaded and may have tether-attachment or tether—capture mechanisms built into the tethering face of the anchor(s). Anchors may also have in-growth material, such as polyester fibers, to promote in-growth of the anchors into the myocardium.

In one embodiment, where a prosthetic heart valve may or may not include a ventricular collar, the anchor or dart is not attached to a lower ventricular collar, but is attached directly into annular tissue or other tissue useful for anchoring.

Tube and/or Cover Material—Biological Tissue—

The tissue used herein is a biological tissue that is a chemically stabilized pericardial tissue of an animal, such as a cow (bovine pericardium) or sheep (ovine pericardium) or pig (porcine pericardium) or horse (equine pericardium). Preferably, the tissue is bovine pericardial tissue. Examples of suitable tissue include that used in the products Dura-guard®, Peri-Guard®, and Vascu-Guard®, all products currently used in surgical procedures, and which are marketed as being harvested generally from cattle less than 30 months old. Other patents and publications disclose the surgical use of harvested, biocompatible animal thin tissues suitable herein as biocompatible "jackets" or sleeves for implantable stents, including for example, U.S. Pat. No. 5,554,185 to Block, U.S. Pat. No. 7,108,717 to Design & Performance—Cyprus Limited disclosing a covered stent assembly, U.S. Pat. No. 6,440,164 to Scimed Life Systems, Inc. disclosing a bioprosthetic heart valve for implantation, and U.S. Pat.

No. 5,336,616 to LifeCell Corporation discloses acellular collagen-based tissue matrix for transplantation.

Polymers

In one preferred embodiment, the conduit may optionally be made from a synthetic material such a polyurethane or polytetrafluoroethylene.

Where a thin, durable synthetic material is contemplated, e.g. for a covering, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

Polyamides (PA)

PA is an early engineering thermoplastic invented that consists of a "super polyester" fiber with molecular weight greater than 10,000. It is commonly called Nylon. Application of polyamides includes transparent tubing's for cardiovascular applications, hemodialysis membranes, and also production of percutaneous transluminal coronary angioplasty (PTCA) catheters.

Polyolefin

Polyolefins include polyethylene and polypropylene are the two important polymers of polyolefins and have better biocompatibility and chemical resistance. In cardiovascular uses, both low-density polyethylene and high-density polyethylene are utilized in making tubing and housings. Polypropylene is used for making heart valve structures.

Polyesters

Polyesters includes polyethylene-terephthalate (PET), using the name Dacron. It is typically used as knitted or woven fabric for vascular grafts. Woven PET has smaller pores which reduces blood leakage and better efficiency as vascular grafts compared with the knitted one. PET grafts are also available with a protein coating (collagen or albumin) for reducing blood loss and better biocompatibility [39]. PET vascular grafts with endothelial cells have been searched as a means for improving patency rates. Moreover, polyesters are widely preferred material for the manufacturing of bioabsorbable stents. Poly-L-lactic acids (PLLA), polyglycolic acid (PGA), and poly(D, L-lactide/glycolide) copolymer (PDLA) are some of the commonly used bioabsorbable polymers.

Polytetrafluoroethylene

Polytetrafluoroethylene (PTFE) is synthetic fluorocarbon polymer with the common commercial name of Teflon by Dupont Co. Common applications of PTFE in cardiovascular engineering include vascular grafts and heart valves. PTFE sutures are used in the repair of mitral valve for myxomatous disease and also in surgery for prolapse of the anterior or posterior leaflets of mitral valves. PTFE is particularly used in implantable prosthetic heart valve rings. It has been successfully used as vascular grafts when the devices are implanted in high-flow, large-diameter arteries such as the aorta. Problem occurs when it is implanted below aortic bifurcations and another form of PTFE called elongated-PTFE (e-PTFE) was explored. Expanded PTFE is formed by compression of PTFE in the presence of career medium and finally extruding the mixture. Extrudate formed by this process is then heated to near its glass transition temperature and stretched to obtain microscopically porous PTFE known as e-PTFE. This form of PTFE was indicated for use in smaller arteries with lower flow rates promoting low thrombogenicity, lower rates of restenosis and hemostasis, less calcification, and biochemically inert properties.

Polyurethanes

Polyurethane has good physiochemical and mechanical properties and is highly biocompatible which allows unrestricted usage in blood contacting devices. It has high shear strength, elasticity, and transparency. Moreover, the surface of polyurethane has good resistance for microbes and the thrombosis formation by PU is almost similar to the versatile cardiovascular biomaterial like PTFE. Conventionally, segmented polyurethanes (SPUs) have been used for various cardiovascular applications such as valve structures, pacemaker leads and ventricular assisting device.

Covered Wire Frame Materials

Drug-eluting wire frames are contemplated for use herein. DES basically consist of three parts: wire frame platform, coating, and drug. Some of the examples for polymer free DES are Amazon Pax (MINVASYS) using Amazonia CroCo (L605) cobalt chromium (Co—Cr) wire frame with Paclitaxel as an antiproliferative agent and abluminal coating have been utilized as the carrier of the drug. BioFreedom (Biosensors Inc.) using stainless steel as base with modified abluminal coating as carrier surface for the antiproliferative drug Biolimus A9. Optima (CID S.r.I.) using 316L stainless steel wire frame as base for the drug Tacrolimus and utilizing integrated turbostratic carbofilm as the drug carrier. VESTA sync (MIV Therapeutics) using GenX stainless steel (316L) as base utilizing microporous hydroxyapatite coating as carrier for the drug Sirolimus. YUKON choice (Translumina) used 316L stainless steel as base for the drugs Sirolimus in combination with Probucol.

Biosorbable polymers may also be used herein as a carrier matrix for drugs. Cypher, Taxus, and Endeavour are the three basic type of bioabsorbable DES. Cypher (J&J, Cordis) uses a 316L stainless steel coated with polyethylene vinyl acetate (PEVA) and poly-butyl methacrylate (PBMA) for carrying the drug Sirolimus. Taxus (Boston Scientific) utilizes 316L stainless steel wire frames coated with translute Styrene Isoprene Butadiene (SIBS) copolymer for carrying Paclitaxel which elutes over a period of about 90 days. Endeavour (Medtronic) uses a cobalt chrome driver wire frame for carrying zotarolimus with phosphorylcholine as drug carrier. BioMatrix employing S-Wire frame (316L) stainless steel as base with polylactic acid surface for carrying the antiproliferative drug Biolimus. ELIXIR-DES program (Elixir Medical Corp) consisting both polyester and polylactide coated wire frames for carrying the drug novolimus with cobalt-chromium (Co—Cr) as base. JACTAX (Boston Scientific Corp.) utilized D-lactic polylactic acid (DLPLA) coated (316L) stainless steel wire frames for carrying Paclitaxel. NEVO (Cordis Corporation, Johnson & Johnson) used cobalt chromium (Co—Cr) wire frame coated with polylactic-co-glycolic acid (PLGA) for carrying the drug Sirolimus.

Examples of preferred embodiments of the reciprocating pressure conduit valve include the following details and features.

Example

The transcatheter prosthetic heart valve may be percutaneously delivered using a transcatheter process via the femoral through the IVC, carotid, sub-xyphoid, intercostal access across the chest wall, and trans-septal to the mitral annulus through the fossa ovalis.

The device is delivered via catheter to the right or left atrium and is expanded from a compressed shape that fits with the internal diameter of the catheter lumen. The compressed valve is loaded external to the patient into the delivery catheter, and is then pushed out of the catheter when the capsule arrives to the atrium. The cardiac treatment technician visualizes this delivery using available imaging techniques such as fluoroscopy or ultrasound.

In a preferred embodiment the valve self-expands upon release from the catheter since it is constructed in part from shape-memory material, such as Nitinol®, a nickel-titanium alloy, or a cobalt-chromium alloy, alloys used in biomedical implants.

In another embodiment, the valve may be constructed of materials that requires balloon-expansion after the capsule has been ejected from the catheter into the atrium.

The atrial collar/frame and the flow control component are expanded to their functional diameter, as they are deployed into the native annulus, providing a radial tensioning force to secure the valve. Once the frame is deployed about the tricuspid annulus, fasteners secure the device about the native annulus. Additional fastening of the device to native structures may be performed, and the deployment is complete. Further adjustments using hemodynamic imaging techniques are contemplated as within the scope of the invention in order to ensure the device is secure, is located and oriented as planned, and is functioning as a substitute or successor to the native tricuspid valve.

Example—Manufacturing Process

In a preferred embodiment the invention includes a process for manufacturing a side delivered transcatheter prosthetic heart valve frame, comprising:
(i) using additive or subtractive metal or metal-alloy manufacturing to produce
a self-expanding annular support frame,
wherein the additive metal or metal-alloy manufacturing is 3D printing or direct metal laser sintering (powder melt), and
wherein the subtractive metal or metal-alloy manufacturing is photolithography, laser sintering/cutting, CNC machining, electrical discharge machining.

In another preferred embodiment, there is provided a process for manufacturing a side delivered transcatheter prosthetic heart valve frame, further comprising the steps of:
(ii) mounting a flow control component within the valve frame, said flow control component configured to permit blood flow along the central vertical axis through an inflow end of the flow control component and block blood flow through an outflow end of the valve, (iii) covering an outer surface of the valve frame with a pericardium material or similar biocompatible material.

Example—Compression Methods

In another preferred embodiment, there is provided a method of compressing, wherein the implantable prosthetic heart valve is rolled or folded into a compressed configuration using a step selected from the group consisting of:
(i) unilaterally rolling into a compressed configuration from one side of the annular support frame;
(ii) bilaterally rolling into a compressed configuration from two opposing sides of the annular support frame;
(iii) flattening the annular support frame into two parallel panels that are substantially parallel to the long-axis, and then rolling the flattened annular support frame into a compressed configuration; and
(iv) flattening the annular support frame along a vertical axis to reduce a vertical dimension of the valve from top to bottom.

DRAWINGS

Figure 1:
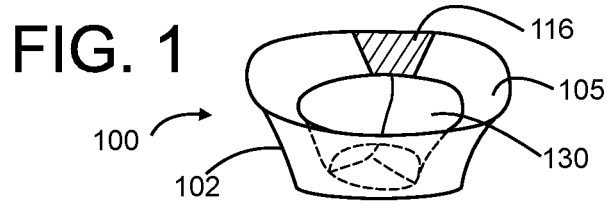
FIG. 1 is an illustration of a SIDE PERSPECTIVE view of a side deliverable transcatheter heart valve with fold area according to the invention.

Referring now to the drawings, FIG. 1 is an illustration of a SIDE PERSPECTIVE view of a side deliverable transcatheter heart valve 100 with fold area 116 according to the invention. FIG. 1 shows a (distal) fold area 116 in the collar portion 105 that permits compression of the valve without subjecting the annular frame 102 or inner flow control component 130 to damaging compression forces.

Figure 2:
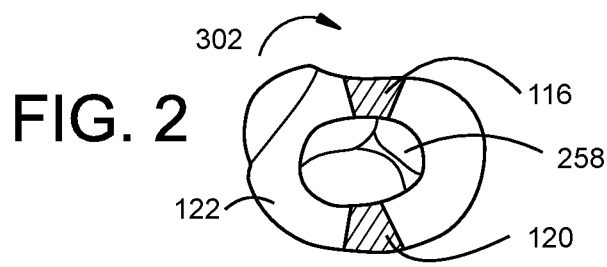
FIG. 2 is an illustration of a SIDE PERSPECTIVE view of the valve showing one side of the valve commence a unilateral rolling process.

FIG. 2 is an illustration of a SIDE PERSPECTIVE view of the valve showing an anterior side 122 of the valve commence a unilateral rolling process 302. FIG. 2 shows two fold areas, proximal (near) 120 and distal (far) 116. The fold areas 116, 120 may be devoid of wire cells or may consist of cells that are large or oriented to minimize the folding or rolling damage from the compression process. Leaflets 258 of the flow control component are visible from this angle.

Figure 3:
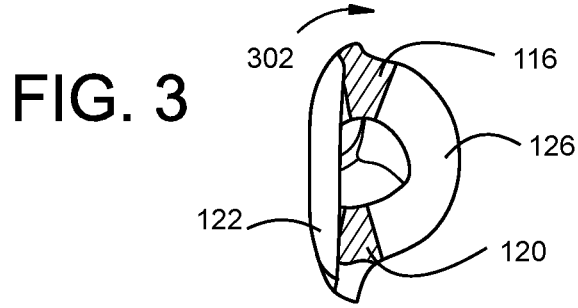
FIG. 3 is an illustration of a SIDE PERSPECTIVE view of the valve showing a second rolling step of a unilateral rolling process.

FIG. 3 is an illustration of a SIDE PERSPECTIVE view of the valve showing a second rolling step of a unilateral rolling process 302. Anterior collar 122 is rolled over to the central distal fold 116 and proximal fold 116 with posterior-septal collar 126 in an unrolled expanded configuration.

Figure 4:
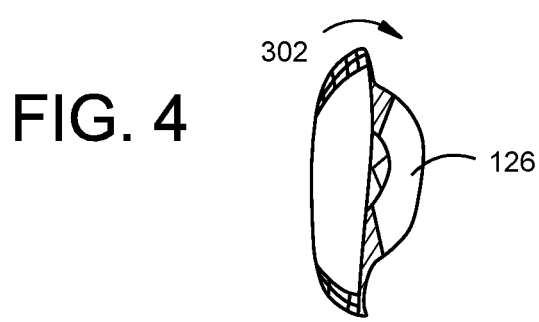
FIG. 4 is an illustration of a SIDE PERSPECTIVE view of the valve showing a third rolling step of a unilateral rolling process.

FIG. 4 is an illustration of a SIDE PERSPECTIVE view of the valve showing a third rolling step of a unilateral rolling process 302. The valve continues to be roll compressed towards the posterior-septal collar 126.

Figure 5:
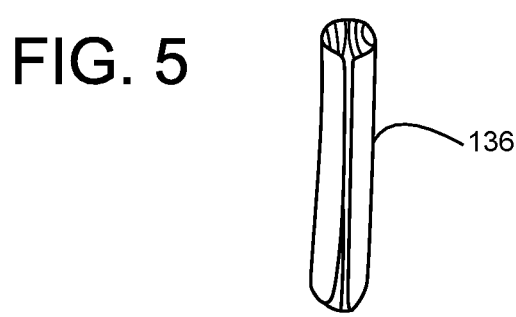
FIG. 5 is an illustration of a SIDE PERSPECTIVE view of the valve showing a completion of the unilateral rolling process.

FIG. 5 is an illustration of a SIDE PERSPECTIVE view of the valve showing a completion of the unilateral rolling process to achieve a roll compressed configuration 136.

FIG. 6 is an illustration of a SIDE VIEW of a compressed valve within a delivery catheter 138. FIG. 6 shows how a central tube or wire 310 can be distally attached to the distal edge or RVOT tab 118 and by pushing on the rigid tube or wire 310, the compressed valve 136 can be pulled from the end closest to the catheter 138 deployment end 139. This pulling action avoids pushing the valve out of the delivery catheter 138, causing additional radial expansion and radial forces that can damage the valve when it is compressed within the delivery catheter 138.

FIG. 7 is an illustration of a SIDE VIEW of a partially compressed valve 402, that is partially released from the delivery catheter 138 and shows how blood flow can begin its transition. The gradual, smooth transition from native flow to flow through the prosthesis by pulling on the rigid pusher 310 attached to the distal subannular anchoring tab 268 avoids the sphincter effect where the heart is cut off from the flow, resulting in a dry pump action, and causing heart failure. When the valve is partially open exposing only a part of the collar 105, only a small fraction of right atrial blood flow is going through the prosthetic valve, but the washing effect provides for a smooth transition to a larger volume going through the prosthesis.

FIG. 8 is an illustration of a SIDE VIEW of a partially compressed valve 402, that is partially released from the delivery catheter 138 and shows how blood flow can begin its transition. The gradual, smooth transition from native flow to flow through the prosthesis from an inflow end 132 to an outflow end 134 by pulling from the distal subannular anchoring tab 268 avoids the sphincter effect where the heart is cut off from the flow, resulting in a dry pump action, and causing heart failure. When the valve is partially open exposing only a part of the collar 105, only a small fraction of right atrial blood flow is initially going through the prosthetic valve, with an increasing amount transitioning from flow around the valve to flow going through the valve, with the washing effect providing for a smooth transition to a larger volume going through the prosthesis.

FIG. 9 is an illustration of a SIDE VIEW of an expanded uncompressed valve orthogonally released from the delivery catheter 138, and still releasably attached to the distal pull wire/deployment control wire or hypotube 310 via the distal tab/RVOT tab 268. Collar 105 and frame body 106 are fully expanded permitting functioning of the flow control component 130. FIG. 9 shows that the valve can be positioned or re-positioned using the rigid pull wire 310. Since the blood flow is not blocked, this allows the interventionalist the opportunity and time to ensure correct orientation of the valve, especially where the distal tab (mitral)/RVOT tab (tricuspid) embodiment is used to assist in anchoring. Once proper orientation is achieved, the valve can be slowly seated into the native tricuspid annulus, providing a smooth blood flow transition from the native flow to the prosthetic flow. FIG. 9 also shows release mechanism 410 for releasing the rigid pull device 310 from the valve body by pulling on a trigger wire that is attached to a release hook, lock, bead, or other mechanism.

FIG. 10 is an illustration of a SIDE VIEW of an uncompressed valve showing transition to all blood flow through the flow control component 130 of the valve and no flow around the valve during to atrial sealing of the anterior collar 122 and posterior-septal collar 126.

Figure 11:
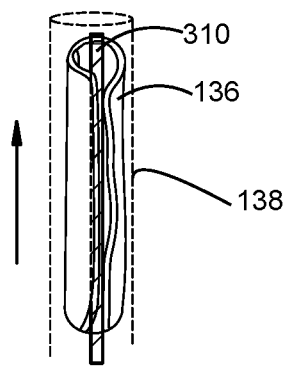
FIG. 11 is an illustration of a SIDE view of a rolled valve within a delivery catheter and being advanced by a distal pull wire/draw-wire (or far-side push-pull wire) attached to the leading edge of the valve collar.

FIG. 11 is an illustration of a SIDE view of a rolled valve 136 within a delivery catheter 138 and being advanced by a distal rigid pull wire/draw-wire 310 (or far-side push-pull wire) attached to the leading edge of the valve collar.

Figure 12:
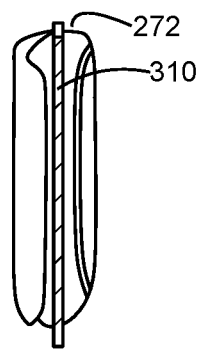
FIG. 12 is an illustration of a SIDE view of a partially unrolled valve that has been deployed from the catheter.

FIG. 12 is an illustration of a SIDE view of a partially unrolled valve that has been deployed from the catheter by action of the pushing rod 310 on the distal upper edge 272.

Figure 13:
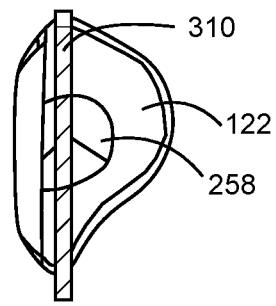
FIG. 13 is an illustration of a SIDE view of a partially released unrolled valve that has been deployed from the catheter.

FIG. 13 is an illustration of a SIDE view of a partially released unrolled valve that has been deployed from the catheter, and shows pushing rod 310 maintaining connection to the valve while anterior collar portion 122 is unrolled and leaflets 258 are uncovered.

Figure 14:
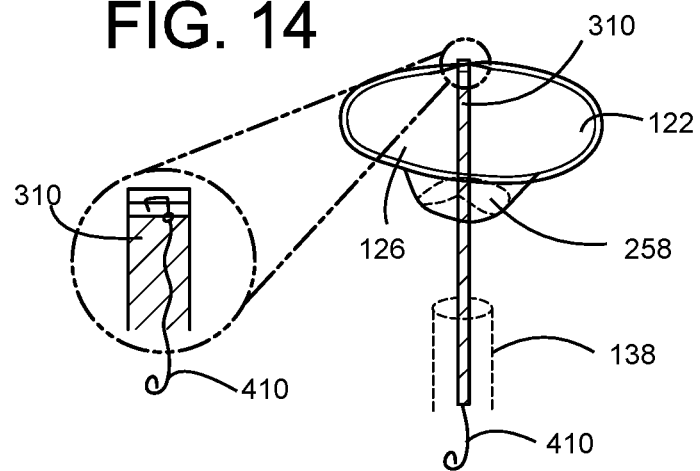
FIG. 14 is an illustration of a SIDE view of a completely released unrolled valve where the wire attachment is used to position the valve within the native annulus.

FIG. 14 is an illustration of a SIDE view of a completely released unrolled valve where the rigid pull device 310 is used to position the valve within the native annulus and obtain a good perivalvular seal with anterior collar 122 and posterior-septal collar 126 to transition to blood flow through the prosthetic leaflets 258. FIG. 14 also shows release mechanism 410 for releasing the rigid pull device 310 from the valve body by pulling on a trigger wire that is attached to a release hook, lock, bead, or other mechanism.

Figure 15:
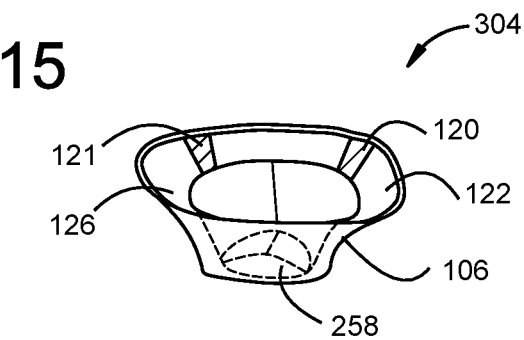
FIG. 15 is an illustration of a SIDE PERSPECTIVE view of the valve showing two (2) sides of the valve commence a bilateral rolling process, with two of four (shown) fold areas.

FIG. 15 is an illustration of a SIDE PERSPECTIVE view of the valve showing two (2) sides of the valve commence a bilateral rolling process 304, with two of four (shown) fold areas, distal fold 120 and second distal fold 121. Anterior collar 122 and posterior-septal collar 126 are shown with outer frame wall 106 and leaflets 258 in dashed line for reference.

Figure 16:
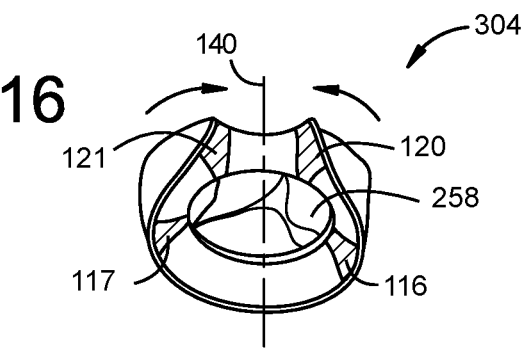
FIG. 16 is an illustration of a SIDE PERSPECTIVE view of the valve showing a second rolling step of a bilateral rolling process.

FIG. 16 is an illustration of a SIDE PERSPECTIVE view of the valve showing a second rolling step of a bilateral rolling process 304. The rim of the annular support frame is shown rolling inward towards the horizontal axis 140. Distal fold 120 and second distal fold 121 are shown opposite from proximal fold area 116 and second proximal fold area 117. Flow control leaflets 258 are shown for reference.

Figure 17:
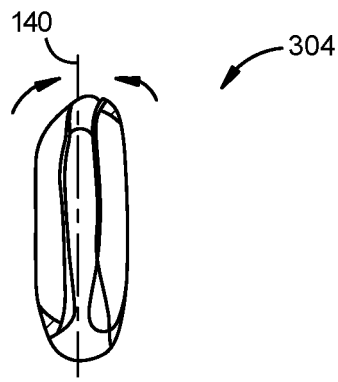
FIG. 17 is an illustration of a SIDE PERSPECTIVE view of the valve showing a third rolling step of a bilateral rolling process.

FIG. 17 is an illustration of a SIDE PERSPECTIVE view of the valve showing a third rolling step of a bilateral rolling process 304. Here, the rolled rim is further rolled inward towards the horizontal axis 140.

Figure 18:
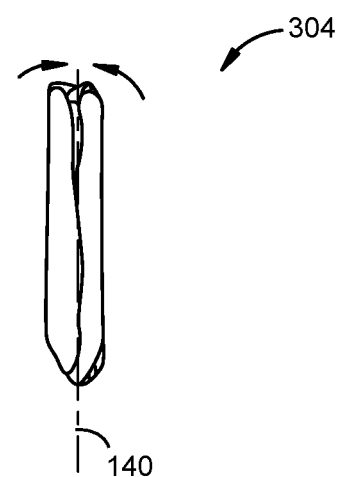
FIG. 18 is an illustration of a SIDE PERSPECTIVE view of the valve showing a completion of the bilateral rolling compression process.

FIG. 18 is an illustration of a SIDE PERSPECTIVE view of the valve showing a completion of the bilateral rolling compression process 304 shown rolled inward towards the horizontal axis 140. FIG. 18 shows a roll-compressed valve as it would appear in a compressed configuration within a delivery catheter (not shown).

Figure 19:
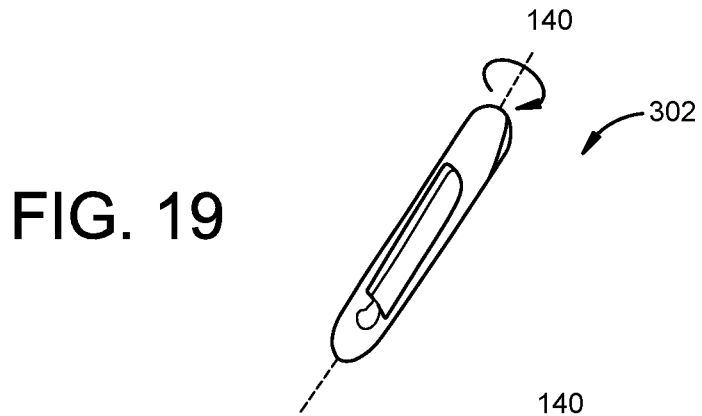
FIG. 19 is an illustration of a SIDE PERSPECTIVE view of a compressed valve where compression used both rolling and folding.

FIG. 19 is an illustration of a SIDE PERSPECTIVE view of a compressed valve where orthogonal compression uses both rolling and folding 302. The lower portion is rolled, and the upper collar portion is folded length-wise around a horizontal axis 140.

Figure 20:
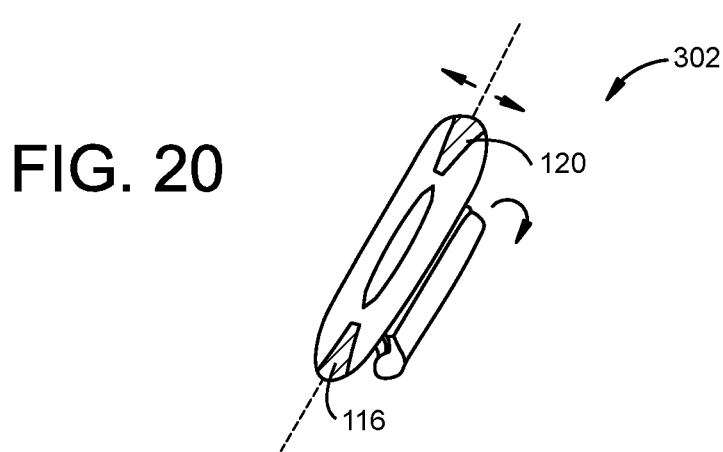
FIG. 20 is an illustration of a SIDE PERSPECTIVE view of a partially uncompressed valve showing unrolling of the lower body portion and unfolding of the flattened upper collar portion.

FIG. 20 is an illustration of a SIDE PERSPECTIVE view of a partially uncompressed valve showing unrolling of the lower body portion and unfolding of the flattened upper collar portion. FIG. 20 shows the fold areas 116, 120 in the collar portion.

Figure 21:
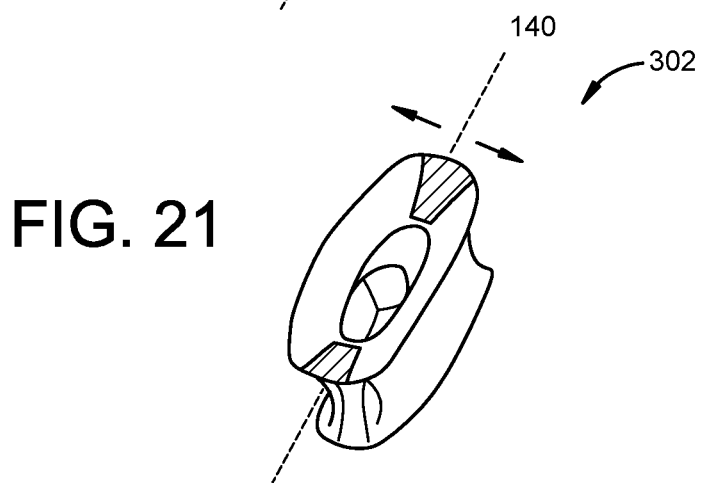
FIG. 21 is an illustration of a SIDE PERSPECTIVE view of the valve showing an uncompressed valve showing an unrolled lower body portion and an unfolded upper collar portion.

FIG. 21 is an illustration of a SIDE PERSPECTIVE view of the valve showing an uncompressed valve showing an unrolled lower body portion and an unfolded upper collar portion. Fold areas in the collar are wider as the valve assumes its expanded configuration.

Figure 22:
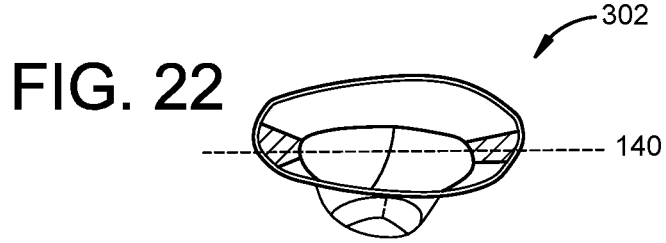
FIG. 22 is an illustration of a SIDE PERSPECTIVE view of the uncompressed valve showing a different side/orientation.

FIG. 22 is an illustration of a SIDE PERSPECTIVE view of the uncompressed valve showing a different side/orientation which is 90 degrees from the prior views.

Figure 23:
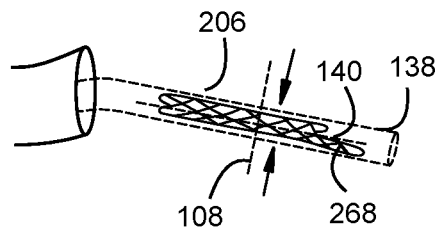
FIG. 23 is an illustration of a SIDE PERSPECTIVE view of a valve that is vertically compressed without folding and loaded into a delivery catheter.

FIG. 23 is an illustration of a SIDE PERSPECTIVE view of a valve that is vertically compressed 206 without folding and loaded into a delivery catheter 138. By using horizontal rather than tradition vertical diamond shaped cells, the frame can be compressed from top to bottom. For example, the valve is compressible along a central vertical axis 108 to the compressed configuration with a horizontal/long-axis 140 being oriented at an intersecting angle of between 45-135 degrees to the central vertical axis 108. This allows for orthogonal delivery of a much larger diameter valve than can be delivered using traditional axial compression. Additionally, the orthogonal delivery provides access from the IVC to the tricuspid annulus using a subannular distal-side anchoring tab 268. Normally, a traditional axial valve would need to make a 90-120 degree right turn before expelling the transcatheter valve. By providing a valve that can be directly expelled into the distal side of the tricuspid annulus, the sharp right turn is avoided due to the inventive design.

Figure 24:
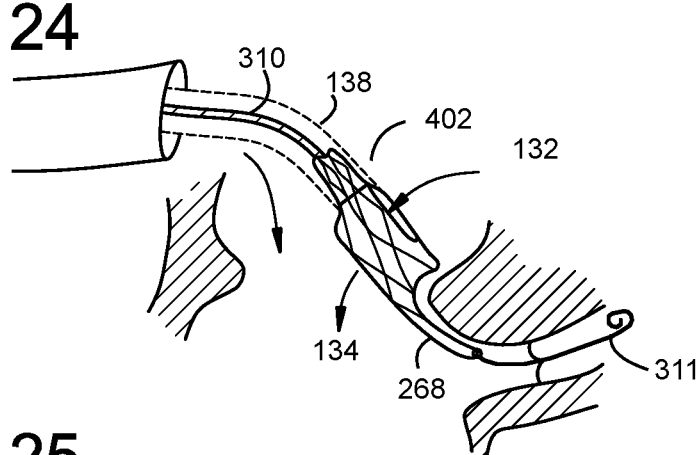
FIG. 24 is an illustration of a SIDE PERSPECTIVE view of a partially expelled or released valve that allows a transition from native blood flow through the native tricuspid valve to a partial flow around the prosthetic valve and into the native annulus and a partial flow thru the prosthetic valve into the native annulus.

FIG. 24 is an illustration of a SIDE PERSPECTIVE view of a partially expelled or released valve 402 from a delivery catheter 138 that allows a transition from native blood flow through the native tricuspid valve to a partial flow around the prosthetic valve and into the native annulus and a partial flow thru an inflow end 132 and out of an outflow end 134 of the prosthetic valve into the native annulus. Guide wire 311 is shown pig-tailed into the pulmonary artery. The rigid pull rod/wire 310 in some embodiments is engineered to ride over the guide wire, thus allowing the valve to be delivered exactly where intended. The distal subannular tab 268 can be directed into the right ventricular outflow tract (RVOT) and provides anchoring to the valve while it is being positioned and assessed.

FIG. 25 is an illustration of a SIDE PERSPECTIVE view of a fully expelled or released valve from a delivery catheter 138 that is lodged using the distal tab 268 against the distal surface of the annulus and held using the rigid pusher 310 elevated at an angle above the native annulus prior to complete deployment. This allows a further transition from native blood flow through the native tricuspid valve with a partial flow around the prosthetic valve and into the native annulus, and an increasing partial flow in a direction along the central axis 108 thru an inflow end 132 and out of an outflow end 134 of the prosthetic valve into the native annulus. FIG. 25 also shows guide wire 311 and proximal side subannular anchoring tab (proximal tab) 270.

FIG. 26 is an illustration of a SIDE PERSPECTIVE view of a fully expelled or released valve 100 that is completely seated into the native annulus, and that allows a smooth transition from native blood flow to a full, complete flow thru the prosthetic valve into the native annulus. The valve is anchored using subannular distal tab 268 and subannular proximal tab 270, and supra-annular (atrial) upper tension arm 271. Corrected replacement flow is shown by flow thru an inflow end 132 and out of an outflow end 134 of the prosthetic valve into the native annulus.

FIG. 27 is an illustration of a SIDE PERSPECTIVE view of a valve that is vertically compressed 206 without folding and loaded into a delivery catheter 138, and shows an extended inner leaflet component in a rolled configuration. Guide wire 311 and RVOT tab 268 are shown extended into the pulmonary artery and allowing the valve to be precisely delivered. 319. FIG. 28 is an illustration of a SIDE PERSPECTIVE view of a partially expelled or released valve 402 from a delivery catheter 138, with a partially unfurled extended inner leaflet component 258. FIG. 28 shows a transition from native blood flow through the native tricuspid valve to a partial flow around the prosthetic valve and into the native annulus and a partial flow 132, 134 thru the prosthetic valve into the native annulus. The valve has a distal mid-wall arch above the RVOT tab 268 for engaging the native annulus.

FIG. 29 is an illustration of a SIDE PERSPECTIVE view of a fully expelled or released valve, with a fully unfurled extended inner leaflet component 258, where the valve is lodged using the distal tab 268 against the distal surface of the annulus and held using the rigid pusher 310 elevated at an angle above the native annulus prior to complete deployment. This allows a further transition from native blood flow through the native tricuspid valve with a partial flow around the prosthetic valve and into the native annulus, and an increasing partial flow thru an inflow end 132 and out of an outflow end 134 of the prosthetic valve into the native annulus. FIG. 29 shows distal mid-wall arch engaging the distal native annulus and shows proximal mid-wall arch raised above the native annulus in preparation for a smooth transition to prosthetic flow when the valve is seated in the native annulus.

FIG. 30 is an illustration of a SIDE PERSPECTIVE view of a fully expelled or released valve 100 that is completely seated into the native annulus, and that allows a smooth transition from native blood flow to a full, complete flow thru the prosthetic valve into the native annulus. The valve is anchored using subannular distal tab 268 and subannular proximal tab 270, and supra-annular (atrial) upper tension arm 271. Corrected replacement flow through leaflets 258 is shown by flow thru an inflow end 132 and out of an outflow end 134 of the prosthetic valve into the native annulus.

FIG. 31 is an illustration of a SIDE PERSPECTIVE view of a valve having a circular hyperboloid (hourglass) shape. Wire frame details are not shown since in practice the external surface would preferably be covered with Dacron polyester to facilitate in-growth. Distal fold area 120 and proximal fold area 116 are shown book-ending the anterior collar 122 and posterior-septal collar 126 along horizontal axis 140 with front anterior wall 110 and central channel 104 shown, according to the invention.

FIG. 32 is an illustration of a CUT-AWAY view of a valve having a circular hyperboloid (hourglass) shape. FIG. 32 shows that inner leaflet 258 and inner frame of flow control component (not visible) are attached to the inner surface of the annular frame, with collar portion 105 attached to subannular anchor portion 269 via wall portion 106. Here, the flow control component is only attached at the top edge although other non-limiting attachments are contemplated, e.g. mid-wall, multiple attachment points, etc.

FIG. 33 is an illustration of an EXPLODED view of a valve having a funnel collar 122, 126 and cylinder body shape 110, 112. FIG. 33 shows one variation where the wire cell is used to create opposing panels, which are joined using fabric strain minimizing panels at distal 120 and proximal 116 fold areas. FIG. 33 also shows a three-leaflet 258 embodiment mounted on an inner U-shaped wire frame 236

FIG. 34 is an illustration of a SIDE view of a two (2) panel 280, 282 embodiment of the valve. FIG. 34 shows that diamond wire cell 298 for the collar portion may be one large diamond in height, while the lower body portion may be constructed using two smaller diamond wire cells in height. Dashed line illustrates where the inner flow control component is attached but not shown.

FIG. 35 is an illustration of a SIDE view of a roll-compressed two-panel embodiment of the valve 136.

FIG. 36 is an illustration of a SIDE PERSPECTIVE view of a valve having a circular hyperboloid (hourglass) shape with an extended RVOT tab 268. Wire frame details are not shown since in practice the external surface would preferably be covered with Dacron polyester to facilitate in-growth. Distal fold area 120 and proximal fold area 116 are shown book-ending the anterior collar 122 and posterior-septal collar 126 along horizontal axis 140 with front anterior wall 110 and central channel 104 shown, according to the invention.

FIG. 37 is an illustration of a CUT-AWAY view of a valve having a circular hyperboloid (hourglass) shape and RVOT tab 268. FIG. 37 shows that inner leaflet 258 and flow control component inner frame (not visible) are attached to the inner surface of the annular frame, with collar portion 105 attached to subannular anchor portion 268 via wall portion 106. Here, it is only attached at the top edge although other non-limiting attachments are contemplated, e.g. mid-wall, multiple attachment points, etc.

FIG. 38 is an illustration of an EXPLODED view of a valve having a funnel collar 122, 126 and cylinder body shape 110, 112. FIG. 38 shows one variation where the wire cell is used to create the entire opposing panels. FIG. 38 also shows a three-leaflet 258 embodiment mounted on an inner U-shaped wire frame 236.

FIG. 39 is an illustration of a SIDE view of a two (2) panel 280, 282 embodiment of the valve. FIG. 34 shows that wave wire cell 296 for the collar portion may be one large wave cell in height, while the lower body portion may be constructed using one or two smaller wave wire cells in height. Dashed line illustrates where the inner flow control component is attached but not shown.

FIG. 40 is an illustration of a SIDE view of a roll-compressed two-panel embodiment of the valve 136.

FIG. 41 is an illustration of a SIDE PERSPECTIVE view of a valve with a folding gap 116, 120 in the wave wire frame 296. Dashed line illustrates where the inner flow control component is attached but not shown.

FIG. 42 is an illustration of a TOP view of a valve with a folding gap 116, 120 in the wave wire frame 296. Central flow control component opening is shown as a horizontal linear gap 262.

FIG. 43 is an illustration of a SIDE PERSPECTIVE view of a valve with a folding gap 286 in a generic annular support wire frame 222. Dashed line illustrates where an inner frame 236 of the inner flow control component is attached but not shown. Wire frame details are not shown since in practice the external surface would preferably be covered with Dacron polyester 242 to facilitate in-growth.

FIG. 44 is an illustration of a TOP view of a valve with a folding gap 286 in the generic annular support wire frame 222. Central flow control component opening is shown as a three-leaflet structure 258.

FIG. 45 is an illustration of a SIDE PERSPECTIVE view of a valve with a folding gap 286 in the wire frame where the gap is covered with a fabric mesh spanning the gap. Fabric folding panels 284 are illustrated on the proximal and distal sides of the lower body portion. Polyester cover 242 for the body portion of outer frame is also shown.

FIG. 46 is an illustration of a SIDE view of a partially rolled lower body portion 211 of valve frame/sheet. FIG. 46 shows that the lower body portion 211 is unfurled towards the septal leaflet. Native anterior and posterior native leaflets are shown in foreground.

FIG. 47 is an illustration of a SIDE view of a vertically compressible valve with internal non-extending leaflets and compressible orthogonal (wide) cells, in an expanded configuration 144.

FIG. 48 is an illustration of a SIDE view of a vertically compressible valve with internal non-extending leaflets and compressible orthogonal (wide) cells, in a compressed configuration 206.

FIG. 49 is an illustration of a SIDE view of a vertically compressible valve with extended leaflets and compressible orthogonal (wide) cells, in an expanded configuration 144.

FIG. 50 is an illustration of a SIDE view of a vertically compressible valve with extended leaflets and compressible orthogonal (wide) cells, in a compressed configuration 206 where the wire frame is reduced in height and the extended leaflets are rolled up.

FIG. 51 is an illustration of a SIDE PERSPECTIVE view of valve having a flat collar and cylinder body. FIG. 51 shows fold areas 116, 120 in the collar and in the lower body portion.

FIG. 52 is an illustration of a SIDE PERSPECTIVE view of the flattened, partially compressed valve 210. FIG. 52 shows the two sides of the collar slide inward, compressing the fold areas 116, 120, to collapse the central axial opening, while flattening the lower body portion along seam 284.

FIG. 53 is an illustration of a SIDE PERSPECTIVE view of the flattened, partially compressed valve 210 with the lower body portion being compressed by rolling 402.

FIG. 54 is an illustration of a SIDE PERSPECTIVE view of the flattened, partially compressed valve 210 with the lower body portion being completely compressed 211 by rolling up to the collar portion.

FIG. 55 is an illustration of a SIDE PERSPECTIVE view of the flattened, compressed valve 208 with the lower body portion compressed by rolling and folded onto the flattened upper collar.

FIG. 56 is an illustration of a SIDE PERSPECTIVE view of a composite laser-cut workpiece prior to expansion into the valve frame. FIG. 56 shows that a wire loop 300 in combination with a wire mesh or wire braid 288 can be combined in a single wire frame.

FIG. 57 is an illustration of a SIDE PERSPECTIVE view of the composite laser-cut workpiece after expansion into a valve wireframe.

FIG. 57 shows collar having laser-cut wire cells 290, and lower having a wire loop 300.

FIG. 58 is an illustration of a SIDE PERSPECTIVE view of a laser-cut orthogonal cell workpieces prior to expansion into the valve frame panels. FIG. 58 illustrates asymmetric irregular rounded wire cells 301.

FIG. 59 is an illustration of a SIDE PERSPECTIVE view of the laser-cut orthogonal workpieces after expansion into the valve wireframe panels 280, 282, prior to assembly. FIG. 59 shows rounded, horizontally oriented wire cells 303 for minimizing wire strain during folding, rolling and compression.

FIG. 60 is an illustration of a SIDE PERSPECTIVE view of a laser-cut orthogonal cell workpieces with zig-zag/diamond shape cells 298 prior to expansion into the valve frame panels.

FIG. 61 is an illustration of a SIDE PERSPECTIVE view of the laser-cut orthogonal workpieces with zig-zag/diamond shape cells 298 after expansion into the valve wireframe panels 280, 282, prior to assembly. FIG. 61 illustrates diamond-shaped, horizontally oriented wire cells 298 for minimizing wire strain during folding, rolling and compression.

FIG. 62 is an illustration of a SIDE PERSPECTIVE view of valve wireframe panels 280, 282 that are stitched along the side edges 284 to form a three-dimensional valve having an arc-shape collar 122, 126 and a cylinder body with an internal flow control component 130 mounted within the body portion.

FIG. 63 is an illustration of a TOP PERSPECTIVE view of valve wireframe panels that are stitched along the side edges 284 to form a three-dimensional valve having an arc-shape collar 122, 126 and a cylinder body with an internal flow control component 130 mounted within the body portion. Dashed line illustrates where the inner flow control component is attached but not shown.

FIG. 64 is an illustration of a SIDE PERSPECTIVE view of the two-panel embodiment being compressed by rolling 402. FIG. 64 shows two panels, sewn along the joining (stitched, joined) edges 284.

FIG. 65 is an illustration of a SIDE PERSPECTIVE view of a two-panel embodiment rolled 208 at least 1 turn, and up to 1.5 turns, or at least 360 degrees, and up to at least 540 degrees.

FIG. 66 is an illustration of a TOP view of a single sheet 305 of metal or metal alloy with compressible cells cut or formed into a first and second collar panel and a first and second body portion. FIG. 66 shows a cut and fold design. FIG. 66 shows where point A on the lower portion can be folded to point A on the collar, and point B on the lower can be folded to point B on the collar to form a three-dimensional valve structure with partial folding to minimize the requirement for extensive sewing.

FIG. 67 is an illustration of a TOP PERSPECTIVE view of the single sheet valve frame 305 after folding, assembly, and attachment along the open seams.

FIG. 68 is an illustration of a SIDE PERSPECTIVE view of the single sheet valve frame 305 after folding, assembly, and attachment along the open seams.

FIG. 69 is an illustration of a SIDE PERSPECTIVE view of a valve formed from a single continuous wire 300, with an upper collar portion, an hourglass shape for the body portion, and an RVOT tab extending away from the lower edge of the body portion.

FIG. 70 is an illustration of a TOP view of a valve formed from a single continuous wire 300, with an upper collar portion, an hourglass shape for the body portion (not shown), and an RVOT tab extending away from the lower edge of the body portion.

FIG. 71 is an illustration of a SIDE PERSPECTIVE view of a valve formed from a series of horizontal wave-shaped wires 297 connected at connection points, with an upper collar portion, and an hourglass shape for the body portion.

FIG. 72 is an illustration of a SIDE PERSPECTIVE view of a valve formed from a series of (vertical) zigzag-shaped wires 298 connected at connection points, with an upper collar portion, and an hourglass shape for the body portion. Sewing features are shown along the joining edges.

FIG. 73 is an illustration of a SIDE PERSPECTIVE view of a valve formed from a series of wave-shaped wires 296 connected at connection points, with an upper collar portion, an hourglass shape for the body portion, and an RVOT tab extending away from the lower edge of the body portion.

FIG. 74 is an illustration of a SIDE PERSPECTIVE view of a valve formed from a series of horizontal wave-shaped wires 297 connected at connection points, with an upper collar portion, an hourglass shape for the body portion, and an RVOT tab extending away from the lower edge of the body portion. Sewing features are shown along the joining edges.

FIG. 75 is an illustration of a TOP PERSPECTIVE view of a valve upper collar portion formed from a series of fan-shaped asymmetric, irregular rounded cells/wires 303 connected circumferentially to the top peripheral edge of the lower body portion.

FIG. 76 is an illustration of a CUT-AWAY view of a valve upper collar portion formed from a series of fan-shaped asymmetric, irregular rounded cells/wires 303 connected circumferentially to the top peripheral edge of the lower body portion, and shows half of the flow control component mounted with the lower body portion FIG. 77 is an illustration of a SIDE PERSPECTIVE view of an upper cuff or collar in a partially expanded configuration, showing how the elongated fan-shape asymmetric, irregular rounded cells/wires 303 permit elongation and radial compression.

FIG. 78 is an illustration of a SIDE PERSPECTIVE view of a two-panel embodiment of a flow control component.

FIG. 79 is an illustration of a SIDE PERSPECTIVE view of a lower body portion having a braided wire cell construction 296.

FIG. 80 is an illustration of a SIDE PERSPECTIVE view of a lower body portion having a diamond laser-cut wire cell construction 298.

FIG. 81 is an illustration of a SIDE PERSPECTIVE view of a lower body portion having a connected-wave wire cell construction 297.

FIG. 82 is an illustration of a SIDE view of a compressed combination construction valve 307 within a delivery catheter, and shows draw/pulling wire attached to the forward end of the compressed valve to pull the valve out of the catheter.

FIG. 83 is an illustration of a SIDE view of human heart anatomy, with an inset showing the geometric relationship between the inferior vena cava (IVC), the three leaflet cusps of the tricuspid valve—anterior, posterior, septal—the right ventricular outflow tract (RVOT), and the pulmonary artery (PA).

FIG. 84 is an illustration of a SIDE PERSPECTIVE view of a side delivered valve seated with the native tricuspid annulus with collar portion laying atrially above the tricuspid annulus and leaflets, lower body portion extending into and through the annulus to provide corrective hemodynamic flow from the flow control component, and RVOT footer tab and RVOT/PA extender wire.

FIG. 85 is an illustration of a TOP view of flat wire frame of metal or metal alloy having compressible wire cells configured in a strain minimizing orientation to facilitate orthogonal loading and delivery of a prosthetic tricuspid valve. FIG. 85 shows outer wave cells 296 used for a collar portion with inner diamond cells 298 used for a body portion of the outer frame.

FIG. 86 is an illustration of a TOP view of smaller sized flat wire frame of metal or metal alloy having compressible wire cells configured in a strain minimizing orientation to facilitate orthogonal loading and delivery of a prosthetic tricuspid valve. FIG. 86 shows outer wave cells 296 used for a collar portion with inner diamond cells 298 used for a body portion of the outer frame.

FIG. 87 is an illustration of a SIDE PERSPECTIVE view of a wire frame in a funnel configuration (heat set) showing compressible wire cells configured in a strain minimizing orientation to facilitate orthogonal loading and delivery of a prosthetic tricuspid valve. FIG. 87 shows outer diamond cells 298 used for a collar portion with inner diamond cells 298 used for a body portion of the outer frame.

FIG. 88 is an illustration of a SIDE PERSPECTIVE view of a wire frame in a funnel configuration (heat set) showing compressible wire cells configured in a strain minimizing orientation to facilitate orthogonal loading and delivery of a prosthetic tricuspid valve. FIG. 88 shows outer diamond cells 298 used for a collar portion with inner diamond cells 298 used for a body portion of the outer frame.

FIG. 89 is an illustration of a TOP view down the central axis of a wire frame in a funnel configuration (heat set) showing compressible wire cells configured in a strain minimizing orientation to facilitate orthogonal loading and delivery of a prosthetic tricuspid valve. FIG. 89 shows outer wave cells 296 used for a collar portion with inner diamond cells 298 used for a body portion of the outer frame.

FIG. 90 is an illustration of a TOP view of flat wire frame having an RVOT tab of metal or metal alloy having compressible wire cells configured in a strain minimizing orientation to facilitate orthogonal loading and delivery of a prosthetic tricuspid valve. FIG. 90 shows outer diamond cells 298 used for a collar portion with inner wave cells 296 used for a body portion of the outer frame, and diamond cells 298 used for the subannular tab 268.

FIG. 91 is an illustration of a TOP view of a wire frame with RVOT tab in a funnel configuration (heat set) showing compressible wire cells configured in a strain minimizing orientation to facilitate orthogonal loading and delivery of a prosthetic tricuspid valve. FIG. 91 shows outer diamond cells 298 used for a collar portion with inner diamond cells 298 used for a body portion of the outer frame, and diamond cells used for the subannular tab 268.

FIG. 92 is an illustration of a SIDE view of a wire frame with RVOT tab in a funnel configuration (heat set) showing compressible wire cells configured in a strain minimizing orientation to facilitate orthogonal loading and delivery of a prosthetic tricuspid valve. FIG. 92 shows outer diamond cells 298 used for a collar portion with inner diamond cells 298 used for a body portion of the outer frame, and diamond cells used for the subannular tab 268.

FIG. 93 is an illustration of a SIDE PERSPECTIVE view of a wire frame with RVOT tab in a funnel configuration (heat set) showing compressible wire cells configured in a strain minimizing orientation to facilitate orthogonal loading and delivery of a prosthetic tricuspid valve. FIG. 88 shows outer diamond cells 298 used for a collar portion with inner diamond cells 298 used for a body portion of the outer frame, and irregular shaped cells used for the subannular tab 268.

FIG. 94 is an illustration of a SIDE PERSPECTIVE view of a metal alloy sheet that has been etched partially on a single side using photolithography and resistive masks.

FIG. 95 is an illustration of a SIDE PERSPECTIVE view of a metal alloy sheet that has been etched partially in a two-sided configuration using photolithography and resistive masks.

PARTS LIST

Below is provide a parts list in relation to claimed elements. Part numbering may refer to functional components and may be re-used across differing preferred embodiments to aid in uniformly understanding structure-function relationships. To avoid cluttering in drawing sheets, not every number may be added to the drawing sheets, or may be added later during examination as needed.

100 VALVE side delivered transcatheter prosthetic heart valve
102 FRAME a self-expanding annular support frame
104 CHANNEL a central channel and
105 COLLAR
106 (TRANS-ANNULAR) WALL an outer perimeter wall
108 CENTRAL AXIS
110 ANTERIOR WALL
112 POSTERIOR-SEPTAL WALL
114 PROX SIDE
116 PROX FOLD
117 second PROX FOLD
118 DISTAL SIDE
120 DISTAL FOLD
121 SECONDARY DISTAL FOLD
122 ANTERIOR COLLAR
124 ANTERIOR BODY
126 POSTERIOR-SEPTAL COLLAR
128 POSTERIOR-SEPTAL BODY
130 FLOW CONTROL COMPONENT
132 INFLOW END
134 OUTFLOW END
136 COMPRESSED CONFIG
138 DELIVERY CATHETER
139 DELIVERY CATH, distal end
140 HORIZ AXIS a horizontal axis at an intersecting angle of between 45-135 degrees to the central vertical axis
144 EXPANDED CONFIG
146 CYLINDER AXIS
148 a height of about 5-60 mm and
150 a diameter of about 25-80 mm.
202 WIRE CELLS a plurality of compressible wire cells having
204 GEOMETRY orthogonal to central vertical axis minimize wire cell strain
206 VERTICAL COMPRESSED CONFIG a vertical compressed configuration,
208 ROLLED COMPRESSED CONFIG a rolled compressed configuration, or
210 FOLDED COMPRESSED CONFIG a folded compressed configuration.
211 ROLLED FLOW CONTROL rolled lower extended leaflet flow control component
212 a SHAPE OF BODY portion selected from a funnel, cylinder, flat cone, or circular hyperboloid.
220 a braided,
222 wire, or
224 laser-cut wire frame, and said annular support frame is covered
226 a biocompatible material.
228 a side profile of valve body is a flat cone shape
230 a diameter R of 40-80 mm,
232 a diameter r of 20-60 mm, and
234 a height of 5-60 mm.
236 INNER FRAME
238 OUTER SURFACE OF FRAME
240 PERICARDIAL tissue
242 DACRON
244 an hourglass shape having
246 a top diameter R1 of 40-80 mm,
248 a bottom diameter R2 of 50-70 mm,
250 an internal diameter r of 20-60 mm, and
252 a height of 5-60 mm.
254 an internal diameter of 20-60 mm and
256 a height of 10-40 mm, and
258 a plurality of LEAFLETS of pericardial material joined to form
260 a ROUNDED cylinder at an INFLOW END and having
262 a FLAT closable aperture at an OUTFLOW END
264 RIBS
266 TENSION ARM a tension arm extending from a distal side
268 SUBANNULAR ANCHORING TAB
269 ANY SUBANNULAR ANCHORING TAB
270 PROXIMAL TAB
271 UPPER TENSION ARM an upper tension arm attached to
272 a DISTAL UPPER EDGE of the annular support frame
274 RVOT TAB a lower tension arm as an RVOT tab extending from
276 a DISTAL SIDE of the annular support frame
278 TISSUE ANCHOR
280 a first FLAT PANEL and the back wall portion is
282 a second FLAT PANEL,
284 SEAM, HINGE a sewn seam, a fabric panel, or a rigid hinge.
286 a flexible FABRIC SPAN without any wire cells proximal fold area and the distal fold area.
288 braided-wire cells,
290 laser-cut wire cells,
292 photolithography produced wire cells,
294 3D printed wire cells,
296 WAVE SHAPE wire cells formed from intermittently connected single strand wires in a wave shape,
297 HORIZ WAVE SHAPE CELLS
298 ZIG-ZAG/DIAMOND shape
300 SPIRAL OUTER FRAME shape, and combinations thereof.
301 asymmetric, irregular rounded cells, compressed
303 asymmetric, irregular rounded cells, expanded
305 ONE-PIECE FOLDABLE OUTER FRAME
307 COMBINATION OF MULTIPLE CELL TYPES
302 (i) unilaterally rolling into a compressed configuration from one side of the annular support frame;
304 (ii) bilaterally rolling into a compressed configuration from two opposing sides
306 (iii) flattening the annular support frame into two parallel panels long-axis, and then rolling to a compressed
308 (iv) flattening the annular support frame along a vertical axis
310 RIGID PUSH/PULL ROD rigid catheter, valve deployment element
311 GUIDE WIRE 312 a STEERABLE CATHETER along an axis parallel to the plane of the valve annulus
314 a TAPERING FIXTURE or funnel attached to a delivery catheter,
316 a LOADING ACCESSORY
318 PUSHING ROD OR PULLING WIRE FOR LOADING
320 a COMPRESSION ELEMENT on an inner surface of the tapering fixture
402 PARTIAL open configuration
404 EXPANDED UNMOUNTED completely open unmounted configuration
406 MOUNTED EXPANDED mounted valve
408 attachment point
410 release mechanism
412 release wire Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A method for loading a side-deliverable prosthetic heart valve into a delivery catheter, the method comprising:
    folding the valve at a proximal fold area and a distal fold area formed by an annular support frame of the valve, the valve having a long-axis that extends through the proximal fold area and the distal fold area, the valve having a flow control component mounted within a central channel of the annular support frame, the central channel extending along a central axis perpendicular to the long-axis, the flow control component configured to permit blood flow in a first direction through an inflow end of the valve and block blood flow in a second direction, opposite the first direction, through an outflow end of the valve;
    compressing the valve along the central axis after the folding to place the valve in a compressed configuration; and
    loading the valve in the compressed configuration into the delivery catheter such that the valve is in a perpendicular or substantially orthogonal orientation relative to the first direction,
    wherein the valve is compressible to the compressed configuration for introduction into a body using the delivery catheter for implanting at a desired location in the body, the long-axis of the valve in the compressed configuration oriented at an intersecting angle of between 45-135 degrees to the first direction, the valve is expandable to an expanded configuration in which the long-axis is oriented at an intersecting angle of between 45-135 degrees to the first direction,
    wherein the long-axis of the valve in the compressed configuration and when loaded into the delivery catheter is substantially parallel to a length-wise cylindrical axis of the delivery catheter.

2. The method of claim 1, wherein the loading includes attaching a loading accessory to a valve sidewall.

3. The method of claim 2, wherein the loading accessory is a pushing rod.

4. The method of claim 3, further comprising:
    pushing, via the pushing rod, the valve in the compressed configuration into and through a lumen of the delivery catheter.

5. The method of claim 2, wherein the loading accessory is a pulling wire.

6. The method of claim 5, further comprising:
    pulling, via the pulling wire, the valve in the compressed configuration into and through a lumen of the delivery catheter.

7. The method of claim 1, wherein the loading includes attaching a loading accessory to a valve cuff.

8. The method of claim 7, wherein the loading accessory is a pushing rod.

9. The method of claim 8, further comprising:
    pushing, via the pushing rod, the valve in the compressed configuration into and through a lumen of the delivery catheter.

10. The method of claim 7, wherein the loading accessory is a pulling wire.

11. The method of claim 10, further comprising:
    pulling, via the pulling wire, the valve in the compressed configuration into and through a lumen of the delivery catheter.

12. The method of claim 1, wherein the loading includes attaching a loading accessory to a valve tension arm.

13. The method of claim 12, wherein the loading accessory is a pushing rod.

14. The method of claim 13, further comprising:
    pushing, via the pushing rod, the valve in the compressed configuration into and through a lumen of the delivery catheter.

15. The method of claim 12, wherein the loading accessory is a pulling wire.

16. The method of claim 15, further comprising:
    pulling, via the pulling wire, the valve in the compressed configuration into and through a lumen of the delivery catheter.

17. The method of claim 12, wherein the valve tension arm is a distal subannular anchoring tab extending from a distal side of the annular support frame.

18. The method of claim 17, wherein the loading includes loading the valve such that the distal subannular anchoring tab is distal to the flow control component mounted within the annular support frame.

* * * * *